United States Patent
Jaklenec et al.

(10) Patent No.: US 9,649,279 B2
(45) Date of Patent: May 16, 2017

(54) FORTIFIED MICRONUTRIENT SALT FORMULATIONS

(71) Applicants: Massachusetts Institute of Technology, Cambridge, MA (US); Tokitae LLC, Bellevue, WA (US)

(72) Inventors: Ana Jaklenec, Cambridge, MA (US); Xian Xu, Waltham, MA (US); Lowell L. Wood, Jr., Bellevue, WA (US); Philip A. Eckhoff, Kirkland, WA (US); William Gates, Redmond, WA (US); Boris Nikolic, Seattle, WA (US); Robert S. Langer, Newtown, MA (US)

(73) Assignees: Massachusetts Institute of Technology, Cambridge, MA (US); Tokitae LLC, Bellevue, WA (US)

( * ) Notice: Subject to any disclaimer, the term of this patent is extended or adjusted under 35 U.S.C. 154(b) by 0 days.

(21) Appl. No.: 14/572,346

(22) Filed: Dec. 16, 2014

(65) Prior Publication Data
US 2015/0164816 A1 Jun. 18, 2015

Related U.S. Application Data

(60) Provisional application No. 61/916,485, filed on Dec. 16, 2013, provisional application No. 62/036,405, filed on Aug. 12, 2014, provisional application No. 62/066,551, filed on Oct. 21, 2014.

(51) Int. Cl.

| | |
|---|---|
| *A23L 1/304* | (2006.01) |
| *A23L 1/00* | (2006.01) |
| *A61K 47/00* | (2006.01) |
| *A61K 9/50* | (2006.01) |
| *A61K 31/519* | (2006.01) |
| *A61K 47/26* | (2006.01) |
| *A61K 47/36* | (2006.01) |
| *A61K 31/295* | (2006.01) |
| *A61K 33/30* | (2006.01) |
| *A61K 31/07* | (2006.01) |
| *A61K 31/714* | (2006.01) |
| *A61K 31/375* | (2006.01) |
| *A61K 31/593* | (2006.01) |
| *A61K 33/18* | (2006.01) |
| *A23P 10/30* | (2016.01) |
| *A23L 27/00* | (2016.01) |
| *A23L 33/10* | (2016.01) |
| *A23L 33/15* | (2016.01) |
| *A23L 33/155* | (2016.01) |
| *A23L 33/16* | (2016.01) |

(52) U.S. Cl.
CPC ............ *A61K 9/5073* (2013.01); *A23L 27/72* (2016.08); *A23L 27/74* (2016.08); *A23L 33/10* (2016.08); *A23L 33/15* (2016.08); *A23L 33/155* (2016.08); *A23L 33/16* (2016.08); *A23P 10/30* (2016.08); *A61K 9/501* (2013.01); *A61K 9/5026* (2013.01); *A61K 31/07* (2013.01); *A61K 31/295* (2013.01); *A61K 31/375* (2013.01); *A61K 31/519* (2013.01); *A61K 31/593* (2013.01); *A61K 31/714* (2013.01); *A61K 33/18* (2013.01); *A61K 33/30* (2013.01); *A61K 47/26* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,182,778 A | 1/1980 | Hall | |
| 4,723,958 A * | 2/1988 | Pope | A61M 31/002 424/438 |
| 5,225,238 A | 7/1993 | Ardaillon | |
| 5,840,329 A * | 11/1998 | Bai | A61K 9/5084 424/457 |
| 6,521,608 B1 * | 2/2003 | Henner | A61K 31/593 514/167 |
| 7,955,619 B2 * | 6/2011 | Shah | A61K 9/2081 424/400 |
| 2003/0152629 A1 | 8/2003 | Shefer | |

FOREIGN PATENT DOCUMENTS

| | | |
|---|---|---|
| CA | 2238925 | 11/1999 |
| WO | 2005055986 | 6/2005 |
| WO | 2012168882 | 12/2012 |

OTHER PUBLICATIONS

Evonik Industries, Dec. 15, 2012, obtained online at: http://eudragit.evonik.com/sites/lists/HN/Documents/evonik-brochure-eudragit-EN.pdf, downloaded on: Apr. 12, 2016.*

(Continued)

*Primary Examiner* — Abigail Fisher
(74) *Attorney, Agent, or Firm* — Pabst Patent Group LLP

(57) ABSTRACT

Salt formulations, which are resistant to moisture and cooking conditions, are described herein. The formulations provide particles of micronutrients and vitamins encapsulated within heat resistant pH-sensitive water-insoluble polymers, which are packaged within a salt shell. The pH-sensitive, water-insoluble, thermally stable materials stabilize the micronutrients, particularly at high temperatures, such as during food preparation and cooking, and release the micronutrients at the desired locations such as the stomach, small intestine, etc. Preferred pH-sensitive polymers release at a low pH, less than the pH present in the stomach. The particles can be used to deliver daily-recommended doses of micronutrients simultaneously with salt, eliminating the need for vitamin pills. This is particularly important in populations suffering from severe malnutrition.

18 Claims, 13 Drawing Sheets

(56) References Cited

OTHER PUBLICATIONS

Google date stamp data for Eduragit product brochure, downloaded on Sep. 5, 2016, pp. 1-2/.*
Vinodkumar, et al., "Impact of a multiple-micronutrient fortified salt on the nutritional status and memory of schoolchildren", Int. J. Vitam. Nutr. Res., 79(5):348-61 (2009).
International Search Report for corresponding Application PCT/US/2014/070583 mailed May 29, 2015.

* cited by examiner

1% EPO Coating (25°C)

10% EPO Coating (25°C)

5% EPO In SGF

FORTIFIED MICRONUTRIENT SALT FORMULATIONS

CROSS-REFERENCE TO RELATED APPLICATIONS

This application claims benefit of U.S. Provisional Application No. 61/916,485, filed Dec. 16, 2013, U.S. Provisional Application No. 62/036,405, filed Aug. 12, 2014, and U.S. Provisional Application No. 62/066,551, filed Oct. 21, 2014. Application No. 61/916,485, filed Dec. 16, 2013, Application No. 62/036,405, filed Aug. 12, 2014, and Application No. 62/066,551, filed Oct. 21, 2014, are hereby incorporated herein by reference in their entirety.

FIELD OF THE INVENTION

This invention is in the field of fortified salts, particularly micronutrient fortified salts that are thermally stable and release the micronutrients at the desired location in the gastrointestinal tract.

BACKGROUND OF THE INVENTION

Malnutrition/micronutrient deficiency is a severe problem in the developing world, impacting 870 million people and causing five million child deaths each year. Attempts to address micronutrient deficiency include supplementation and fortifications. Supplementation can provide higher doses of micronutrients to specific individuals in a short amount of time. However, supplementation has limitations, including inability to deliver all the necessary micronutrients, neglecting individuals in non-targeted groups, and low compliance due to the difficulty in storing product under uncontrolled conditions (hot wet warehouses, poor record keeping), difficulties in distributing supplements and convincing end users of the need for regular ingestion.

Food fortification has been explored as a means for addressing malnutrition/micronutrient deficiency. However, food fortification is often unaffordable to those people who need it most. Adverse effects, such as sensory qualities of foods, adverse nutrient-nutrient interactions, and poor bioavailability, have also been observed in fortified foods.

Salt is a universally consumed product and therefore has the potential to deliver vitamins and minerals to those in developing countries. Fortified salt, also known as iodized salt, is table salt (NaCl) mixed with minute amounts of various salts of iodide, to prevent iodine deficiency. Double fortified salt, which is table salt containing iron and iodide has also been developed. The iron is microencapsulated with stearine to prevent it from reacting with the iodine in the salt. However, adding iron to iodized salt is complicated by a number of chemical, technical, and organoleptic issues, including the tendency of iron to oxide in the presence of air. Salt has also been fortified with potassium fluoride in an attempt to enhance dental health. None of these fortified salts include more labile supplements such as vitamins.

All of these formulations involve physical mixing of salt with one or more minerals. However, as discussed above, the undesirable reactivity between vitamins and minerals and other limitations have prevented commercialization of such formulations. Moreover, these formulations do not provide a plurality of micronutrients and are not stable under conditions encountered during food preparation and cooking.

Kwan describes a fortified salt containing vitamin A, iron, and iodine. The formulation is a physical mixture of salt and forticants. The formulation also contains surfactants and lipids so that the formulation self-emulsifies. Kwan discloses that an attempt was made to enteric coat vitamin A, but losses of the micronutrient after a three month storage period ranged from 50-99% at both 25° C./20% RH and 45° C./60% RH.

Health Salt, sold by Sundar, is a fortified salt containing a plurality of micronutrients, which is allegedly thermally stable. The formulation appears to be a physical mixture of salt and the various micronutrients. Vinodkumar et al., *Int. J. Vitam. Nutr. Res.*, 79(5):348-361 (2009), describes manufacturing a multiple micronutrient-fortified salt in a ribbon blender and evaluating the homogeneity of the distribution of the micronutrients in the salt. However, the product costs 2-3 times more than loose salt, black specks of forticants were observed in the product which may turn off consumers, the product had an unusual odor, and it may be difficult to verify analytically some of the micronutrients in the product.

There exists a need for compositions that provide a plurality of micronutrients in a safe and effective manner while overcoming the limitations of supplementation and fortification discussed above.

Therefore, it is an object of the invention to provide compositions for providing a plurality of heat, moisture and salt labile micronutrients, as well as therapeutic and/or prophylactic agents, and methods of making and using thereof.

It is a further object of the invention to provide compositions for providing a plurality of micronutrients, which are stable during food preparation and cooking, and methods of making and using thereof.

It is a still further object of the invention to provide compositions for providing a plurality of micronutrients, which are stable during food preparation and cooking, and which release the micronutrients at a desired site in the gastrointestinal tract, and methods of making and using thereof.

SUMMARY OF THE INVENTION

Formulations which are resistant to moisture and cooking temperatures, and release at a defined pH range, have been developed. The formulations provide particles of micronutrients and vitamins ("MNs") formulated into a stabilizing matrix formed of materials such as sugars, which is then encapsulated within heat resistant pH-sensitive water-insoluble polymers. The formulation can be packaged within a salt shell, sugar shell, or other shell. The pH-sensitive, water-insoluble, thermally stable polymers stabilize the micronutrients, especially in combination with the salt, particularly at high temperatures, such as during food preparation and cooking, and release the micronutrients at the desired locations such as the stomach, small intestine, etc. Preferred pH-sensitive polymers release at a low pH, such as pH 1-3, preferably 1-2 as found in the stomach. The particles can be used to deliver daily-recommended doses of micronutrients simultaneously with salt or other shell substance, eliminating the need for other vitamin supplementation. This is particularly important in populations suffering from severe malnutrition. The same technology can be used to deliver therapeutic, prophylactic or diagnostic agents, for example, anti-parasitic agents. Advantages of this formulation include heat and moisture stability, as well as being uniformly colored and relatively odorless.

A delivery platform consisting of a hyaluronic acid (HA) hydrogel particle (HGP)-based core for MNs encapsulation, and a low-pH-soluble and thermostable microsphere (MS) jacket surrounding the HGPs for protection was developed.

The MS jacket can be encased by sodium chloride, yielding MNs fortified salt. The MS jacket can also be encased in another substance, such as sugar. Alternatively, the MS jacket can be used uncoated. The system is shown to efficiently encapsulate MNs, maintain their stability under cooking conditions, and release the payload in simulated gastric fluid (SGF) with desired release profiles.

The same technology is also advantageous in providing weather and heat resistant vitamin and mineral formulations for agricultural applications, such as livestock supplementation for ruminants (rumen pH 5.5-6.5). The use of polymers providing specific release based on pH provides a means for targeting release in a particular gastrointestinal region for greatest efficacy of uptake and retention of bioactivity.

DETAILED DESCRIPTION OF THE INVENTION

I. Definitions

Figures 1A, 1B, 1C, 1D:
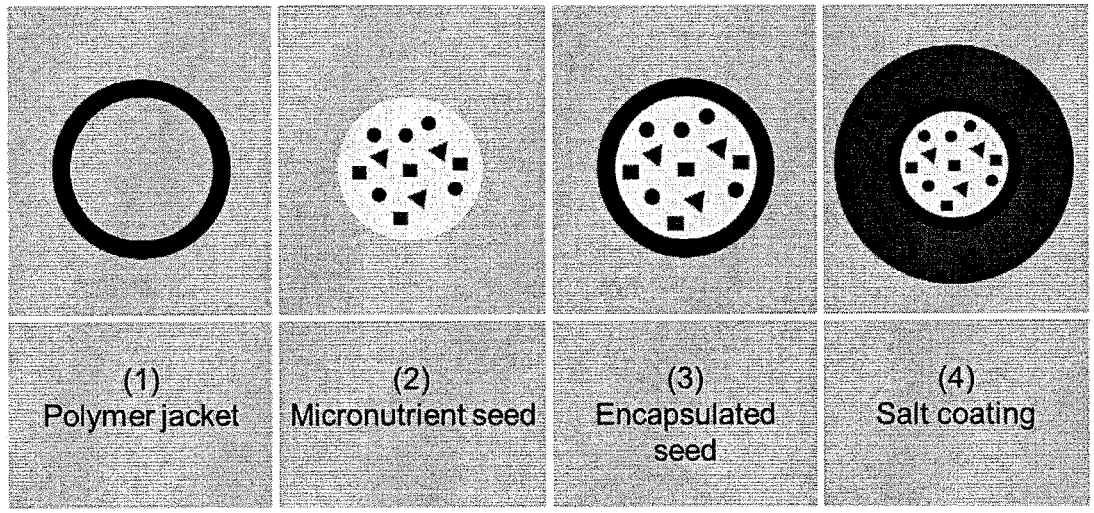
FIGS. 1A-1G is a schematic of the components of the formulations. In one form, polymer jacket (FIG. 1A), core of stabilizing matrix containing micronutrient particles (FIG. 1B), core containing micronutrient particles encapsulated in the polymeric outer layer (FIG. 1C), and polymeric outer layer-encapsulated core containing particles coated with salt (FIG. 1D). In another form, micronutrient seeds (particles) encapsulated in hydrogel matrix (FIG. 1E), hydrogel particles encapsulated in polymer (FIG. 1F), and coated with salt (FIG. 1G).

"pH-sensitive" as used herein generally refers to materials, such as polymers, whose dissolution properties are pH-dependent.

"Water-insoluble", as used herein, as used herein means that a material, such as a polymer, does not dissolve in aqueous solutions or buffers above pH 5.

"Thermally stable" as used herein generally means that a material is chemically and/or physically stable (e.g., does not degrade) at temperatures encountered during food preparation and/or cooking (e.g., up to and including boiling) for a period of at least about ten to twenty minutes, for example, up to about two to about four hours.

"Stable at storage temperature" as used herein generally means that a material is chemically and/or physically stable (e.g., does not degrade) from about −4° C. (e.g., refrigerator temperature) to about 25-35° C., with a humidity of 40-60%.

"Micronutrients" as used herein generally refers to a substance, such as a vitamin or mineral that is essential in minute amounts (e.g., less than 100 mg/day) for the proper growth and metabolism of a living organism, such as a human. "Micronutrients" includes both microminerals or trace elements and microvitamins.

"Non-porous" as used herein generally means a material, such as a polymer, is impermeable to water (e.g., when submerged in it) at room temperature and under cooking conditions for at least 10 minutes, preferably up to at least several days (e.g., a week, two weeks). The material is also impermeable to moisture when stored dry for at least 10 minutes to at least weeks, e.g., one week, two weeks, three week, 4 weeks; 5 weeks, or 6 weeks.

The term "diameter" is art-recognized and is used herein to refer to either of the physical diameter or the hydrodynamic diameter. The diameter of emulsion typically refers to the hydrodynamic diameter. The diameter of the capsules, both in spherical or non-spherical shape, may refer to the physical diameter in the hydrated state. The diameter of the particles, colloids and cells which are encapsulated inside the capsules refers to the physical diameter in the hydrated state. As used herein, the diameter of a non-spherical particle or a non-spherical capsule may refer to the largest linear distance between two points on the surface of the particle. When referring to multiple particles or capsules, the diameter of the particles or the capsules typically refers to the average diameter of the particles or the capsules. Diameter of particles or colloids can be measured using a variety of techniques, including but not limited to the optical or electron microscopy, as well as dynamic light scattering.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "microspheres" or "microcapsules" is art-recognized, and includes substantially spherical solid or semi-solid structures, e.g., formed from biocompatible polymers such as subject compositions, having a size ranging from about one or greater up to about 1000 microns. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm.

"Matrix" as used herein generally refers to one or more solid or semi-solid material in which is embedded one or more others materials.

"Hydrogel" as used herein is a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content II. Formulations Formulations made up of particles distributed in a matrix which is coated or encapsulated with one or more pH-sensitive, water-insoluble, thermally stable materials, encapsulated in a salt, are used for simultaneous delivery of salts, vitamins and trace minerals, and optionally one or more therapeutic, prophylactic, and/or diagnostic agents. The pH-sensitive, water-insoluble, thermally stable materials help to stabilize the vitamins and trace minerals, particularly at high temperatures, such as during preparation and cooking, and effect release of the vitamins and micronutrients at the desired locations after ingestion (e.g., stomach, small intestine, etc.). The particles can be used to deliver daily-recommended dosages of micronutrients via salt, eliminating the need for vitamin pills, or other therapeutic and prophylactic agents. This is particularly important in populations suffering from severe malnutrition in third world countries. In some embodiments, the particles are not self-emulsifying.

As described below, the particles are formed from vitamins and micronutrients. These particles are then dispersed in a stabilizing matrix, formed, by example, of sugars and/or oils. The matrix, preferably regular shaped, such as spherical, is then coated or encapsulated with a pH-sensitive polymer, preferably which forms a water impermeable or having reduced water permeability, which may also act to taste mask the particles. The encapsulated matrix with particles therein is then coated with salt.

In some embodiments, the formulations of particle/matrix coated or encapsulated with a pH-sensitive polymer can be used without a coating of salt or other material.

Figures 1E, 1F, 1G:
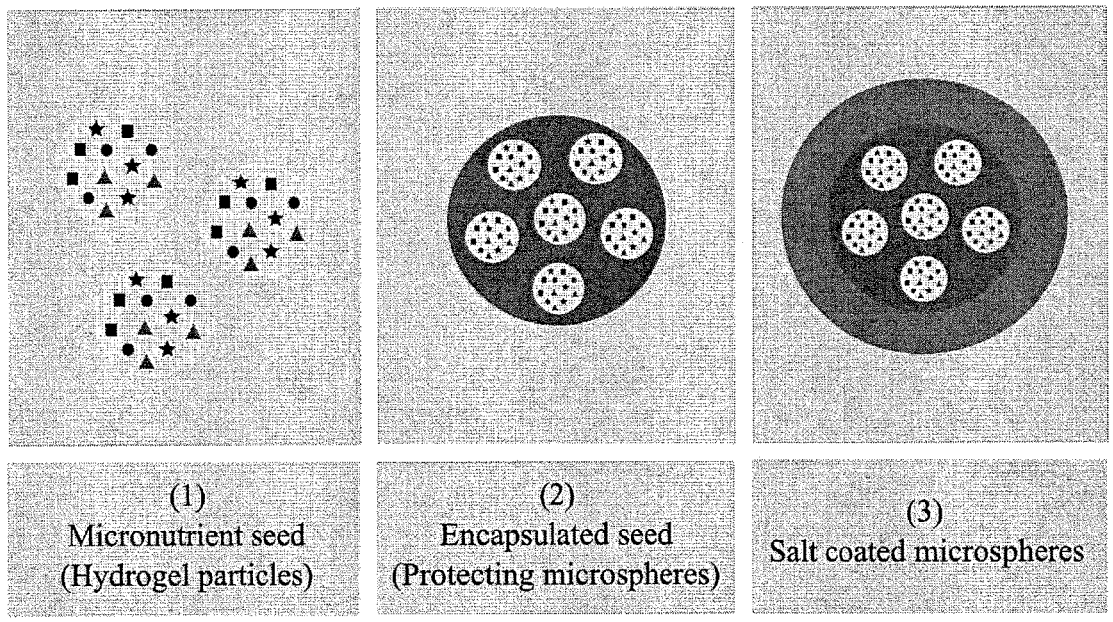

Examples of two forms of the disclosed formulations are illustrated in FIG. 1.

A. Particles

Particles or seeds are formed of the one or more micronutrients, therapeutic, prophylactic, and/or diagnostic agents. The diameter of the particles or seeds can vary. However, in some embodiments, the average diameter is from about a few nanometers up to about 1000 microns, preferably from a few nanometers to about 500 microns. The particles can contain therapeutic agents, prophylactic agents, and/or diagnostic agents, but are most preferably trace minerals and vitamins and/or other micronutrients.

Exemplary micronutrients include, but are not limited to, iron, cobalt, zinc, manganese, copper, iodine, selenium, molybdenum, chromium, vitamin A, beta carotene, vitamin B1, vitamin B2, vitamin B3, vitamin B6, vitamin B9 (folic acid), vitamin B12, vitamin C, vitamin D3, vitamin E, vitamin K, pantothenic acid, biotin, and combinations thereof. The required daily dosage of most micronutrients is less than 100 mg/day. Recommended values are shown in Table 1, from the US Department of Agriculture 2013.

| | | | | | | | | | | | |
|---|---|---|---|---|---|---|---|---|---|---|---|
| Dietary Reference Intakes (DRIs): Estimated Average Requirements Food and Nutrition Board, Institute of Medicine, National Academies | | | | | | | | | | | |
| Life Stage Group | Calcium (mg/d) | CHO (g/d) | Protien (g/kg/d) | Vit A (μg/d)$^a$ | Vit C (mg/d) | Vit D (μg/d) | Vit E (mg/d)$^b$ | Thiamin (mg/d) | Riboflavin (mg/d) | Niacin (mg/d)$^c$ | Vit B$_5$ (mg/d) |
| Infants | | | | | | | | | | | |
| 0 to 6 mo | | | | | | | | | | | |
| 6 to 12 mo | | | 1.0 | | | | | | | | |
| Children | | | | | | | | | | | |
| 1-3 y | 500 | 100 | 0.87 | 210 | 13 | 10 | 5 | 0.4 | 0.4 | 5 | 0.4 |
| 4-8 y | 800 | 100 | 0.76 | 275 | 22 | 10 | 6 | 0.5 | 0.5 | 6 | 0.5 |
| Males | | | | | | | | | | | |
| 9-13 y | 1,100 | 100 | 0.76 | 445 | 39 | 10 | 9 | 0.7 | 0.8 | 9 | 0.8 |
| 14-18 y | 1,100 | 100 | 0.73 | 630 | 63 | 10 | 12 | 1.0 | 1.0 | 12 | 1.1 |

-continued

Dietary Reference Intakes (DRIs): Estimated Average Requirements
Food and Nutrition Board, Institute of Medicine, National Academies

| | | | | | | | | | | |
|---|---|---|---|---|---|---|---|---|---|---|
| 19-30 y | 800 | 100 | 0.66 | 625 | 75 | 10 | 12 | 1.0 | 1.0 | 12 | 1.1 |
| 31-50 y | 800 | 100 | 0.66 | 625 | 75 | 10 | 12 | 1.0 | 1.0 | 12 | 1.1 |
| 51-70 y | 800 | 100 | 0.66 | 625 | 75 | 10 | 12 | 1.0 | 1.0 | 12 | 1.4 |
| >70 y | 1,000 | 100 | 0.66 | 625 | 75 | 10 | 12 | 1.0 | 1.0 | 12 | 1.4 |
| Females | | | | | | | | | | | |
| 9-13 y | 1,100 | 100 | 0.76 | 420 | 39 | 10 | 9 | 0.7 | 0.8 | 9 | 0.8 |
| 14-18 y | 1,100 | 100 | 0.71 | 485 | 56 | 10 | 12 | 0.9 | 0.9 | 11 | 1.0 |
| 19-30 y | 800 | 100 | 0.66 | 500 | 60 | 10 | 12 | 0.9 | 0.9 | 11 | 1.1 |
| 31-50 y | 800 | 100 | 0.66 | 500 | 60 | 10 | 12 | 0.9 | 0.9 | 11 | 1.1 |
| 51-70 y | 1,000 | 100 | 0.66 | 500 | 60 | 10 | 12 | 0.9 | 0.9 | 11 | 1.3 |
| >70 y | 1,000 | 100 | 0.66 | 500 | 60 | 10 | 12 | 0.9 | 0.9 | 11 | 1.3 |
| Pregnancy | | | | | | | | | | | |
| 14-18 y | 1,000 | 135 | 0.88 | 530 | 66 | 10 | 12 | 1.2 | 1.2 | 14 | 1.6 |
| 19-30 y | 800 | 135 | 0.88 | 530 | 70 | 10 | 12 | 1.2 | 1.2 | 14 | 1.6 |
| 31-50 y | 800 | 135 | 0.88 | 550 | 70 | 10 | 12 | 1.2 | 1.2 | 14 | 1.6 |
| Lactation | | | | | | | | | | | |
| 14-18 y | 1,000 | 160 | 1.05 | 885 | 96 | 10 | 16 | 1.2 | 1.3 | 13 | 1.7 |
| 19-30 y | 800 | 160 | 1.05 | 900 | 100 | 10 | 16 | 1.2 | 1.3 | 13 | 1.7 |
| 31-50 y | 800 | 160 | 1.05 | 900 | 100 | 10 | 16 | 1.2 | 1.3 | 13 | 1.7 |

| Life Stage Group | Folate ($\mu$g/d)[d] | Vit $B_{12}$ ($\mu$g/d) | Copper ($\mu$g/d) | Iodine ($\mu$g/d) | Iron (mg/d) | Magnesium (mg/d) | Molybdenum ($\mu$g/d) | Phosphorus (mg/d) | Selenium ($\mu$g/d) | Zinc (mg/d) |
|---|---|---|---|---|---|---|---|---|---|---|
| Infants | | | | | | | | | | |
| 0 to 6 mo | | | | | | | | | | |
| 6 to 12 mo | | | | | 6.9 | | | | | 2.5 |
| Children | | | | | | | | | | |
| 1-3 y | 120 | 0.7 | 260 | 65 | 3.0 | 65 | 13 | 380 | 17 | 2.5 |
| 4-8 y | 160 | 1.0 | 340 | 65 | 4.1 | 110 | 17 | 405 | 23 | 4.0 |
| Males | | | | | | | | | | |
| 9-13 y | 250 | 1.5 | 540 | 73 | 5.9 | 100 | 26 | 1,055 | 35 | 7.0 |
| 14-18 y | 330 | 2.0 | 685 | 95 | 7.7 | 340 | 33 | 1,055 | 45 | 8.5 |
| 19-30 y | 320 | 2.0 | 700 | 95 | 6 | 330 | 34 | 580 | 45 | 9.4 |
| 31-50 y | 320 | 2.0 | 700 | 95 | 6 | 350 | 34 | 580 | 45 | 9.4 |
| 51-70 y | 320 | 2.0 | 700 | 95 | 6 | 350 | 34 | 580 | 45 | 9.4 |
| >70 y | 320 | 2.0 | 700 | 95 | 6 | 350 | 34 | 580 | 45 | 9.4 |
| Females | | | | | | | | | | |
| 9-13 y | 250 | 1.5 | 540 | 73 | 5.7 | 200 | 26 | 1,055 | 35 | 7.0 |
| 14-18 y | 330 | 2.0 | 685 | 95 | 7.9 | 300 | 33 | 1,055 | 45 | 7.3 |
| 19-30 y | 320 | 2.0 | 700 | 95 | 8.1 | 255 | 34 | 580 | 45 | 6.8 |
| 31-50 y | 320 | 2.0 | 700 | 95 | 8.1 | 265 | 34 | 580 | 45 | 6.8 |
| 51-70 y | 320 | 2.0 | 700 | 95 | 5 | 265 | 34 | 580 | 45 | 6.8 |
| >70 y | 320 | 2.0 | 700 | 95 | 5 | 265 | 34 | 580 | 45 | 6.8 |
| Pregnancy | | | | | | | | | | |
| 14-18 y | 520 | 2.2 | 785 | 160 | 23 | 335 | 40 | 1,055 | 49 | 10.5 |
| 19-30 y | 520 | 2.2 | 800 | 160 | 22 | 290 | 40 | 580 | 49 | 9.5 |
| 31-50 y | 520 | 2.2 | 800 | 160 | 22 | 300 | 40 | 580 | 49 | 9.5 |
| Lactation | | | | | | | | | | |
| 14-18 y | 450 | 2.4 | 985 | 209 | 7 | 300 | 35 | 1,055 | 59 | 10.9 |
| 19-30 y | 450 | 2.4 | 1,000 | 209 | 6.5 | 255 | 36 | 580 | 59 | 10.4 |
| 31-50 y | 450 | 2.4 | 1,000 | 209 | 6.5 | 265 | 36 | 580 | 59 | 10.4 |

NOTE:
An Estimated Average Requirement (EAR) is the average daily nutrient intake level estimated to meet the requirements of half of the healthy individuals in a group. EARs have not been established for vitamin K, pantothenic acid, biotin, choline, chromium, fluoride, manganese, or other nutrients not yet evaluated via the DRI process.
[a] As retinal activity equivilents (RAEs) 1 RAE = 1 $\mu$g retinol, 12 $\mu$g $\beta$-carotene, 24 $\mu$g $\alpha$-carotene, or 24 $\mu$g $\beta$-cryptocanthin. The RAE for dietary provitamin A carotenoids is two-fold greater than retinol equivalents (RE), whereas the RAE for preformed vitamin A is the same as RE.
[b] As $\alpha$-tocopherol $\alpha$-Tocopherol includes RRR-$\alpha$-tocopherol, the only form of $\alpha$-tocopherol that occurs naturally in foods, and the 2R-stereoisomeric forms of $\alpha$-tocopherol (RRR-,RSR-, and RSS-$\alpha$-tocopherol) that occurs in fortified foods and supplements. It does not include the 2S- stereoisomeric forms of $\alpha$-tocopherol (SRR-, SSR-, SRS-, and SSS-$\alpha$-tocopherol), also found in fortified foods and supplements.
[c] As niacin equivalents (NE), 1 mg of niacin = 60 mg of tryptophan.
[d] As dietary folate equivalents (DFE). 1 DFE = 1 $\mu$g food folate = 0.6 $\mu$g of folic acid from fortified food or as a supplement consumed with food = 0.5 $\mu$g of a supplement taken on an empty stomach.
Sources: Dietary Reference Intakes for Calcium, Phosphorus, magnesium, Vitamin D, and Fluoride (1997): Dietary Reference Intakes for Thiamin, Riboflavin, Niacin, Vitamin $B_5$, Folate, Vitamin $B_{12}$, Pantothenic Acid, Biotin, and Choline (1998): Dietary Referneve Intakes for VItamin C, Vitamin E, Selenium, and Caroteroids (2000): Dietary Reference Intakes for Vitamin A, Vitamin K, Arsenic, Boron, Chromium, Copper, Iodine, Iron, Manganese, Molybdenum, Nickel, Silicon, Tanadium, and Zinc (2001): Dietary Reference Intakes for Energy, Carbohydrate, Fiber, Fat, Fatty Acids, Cholesterol, Protein, and Amino Acids (2002/2005): and Dietary Reference Intakes for Calcium and Vitamin D (2011). These reports may be accessed via www.nap.edu.

Vitamin A is involved in physiological processes that result in cellular differentiation, cellular maturity, and cellular specificity. Vitamin A is an important component of a nutritional supplement for subjects in physiologically stressful states, such as those caused by pregnancy, lactation or disease state. Vitamin A may be included in the form of acetate. 100% RDA for children 6-59 months old is 0.9 mg/day. 50% RDA for an adult female is 0.45 mg/day. Useful forms of vitamin A for the disclosed formulations include retinyl palmitate, retinyl acetate, and beta-carotene.

Beta-carotene is converted to vitamin A within the body as needed. Beta-carotene also has powerful antioxidant properties. Antioxidants are important during physiologically stressful events for numerous reasons. For example, lipid peroxidation has been associated with over 200 disease processes. Antioxidants are especially important during pregnancy because in the first trimester, establishment of blood flow into the intervillous space is associated with a burst of oxidative stress. The inability to mount an effective antioxidant defense against this burst results in early pregnancy loss. Further, oxidative stress has been implicated in the pathophysiology of preeclampsia, a toxemia of pregnancy. Finally, oxidative stress during pregnancy plays an important role in fetal growth, and healthy antioxidant levels are positively correlated with birth weight and length.

B-complex contains water-soluble nutrients generally not stored in the body. They play roles in a variety of biological processes critical to the health of pregnant women, lactating women, and fetuses such as, for example, the metabolism of homocysteine. The B-complex vitamins contain one or more of vitamin B1, vitamin B2, vitamin B3, vitamin B6, vitamin B9, and vitamin B12. B vitamins often work in concert with each other, and multiple B vitamin deficiencies are assumed more common than single B vitamin deficiencies.

Vitamin B1 plays a role in carbohydrate metabolism and neural function. It is a coenzyme for the oxidative decarboxylation of alpha-ketoacids (e.g., alpha-ketoglutarate and pyruvate) and for transketolase, which is a component of the pentose phosphate pathway. Vitamin B1 may be included in the form of thiamine mononitrate.

Vitamin B2 is a component of two flavin coenzymes, flavin mononucleotide (FMN) and flavin adenine dinucleotide (FAD). These flavoenzymes are involved in a number of oxidation-reduction reactions including the conversion of pyridoxine and niacin. Flavoenzymes also play a role in a number of metabolic pathways such as amino acid deamination, purine degradation and fatty acid oxidation and thus help to maintain carbohydrate, amino acid and lipid metabolism. Vitamin B2 may be included in the form of riboflavin.

Vitamin B3, or "niacin," is the common name for two compounds: nicotinic acid (also called niacin) and niacinamide (also called nicotinamide). Vitamin B3 is important for maintaining healthy levels and types of fatty acids. It is also required for the synthesis of pyroxidine, riboflavin, and folic acid. Administration of vitamin B3 also may effect a reduction in total cholesterol (LDL) and very low-density lipoprotein (VLDL) levels and an increase in high-density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Vitamin B3 may be included in the form of niacinamide. In another embodiment, the formulation may include an equivalent molar amount of niacin.

Vitamin B6 may reduce the levels of homocysteine. The active forms of vitamin B6, pyridoxal-5'-phosphate (PLP) and pyridoxamine-5'-phosphate, are coenzymes for numerous enzymes and as such, are important for gluconeogenesis, niacin formation, and erythrocyte metabolism. Vitamin B6 is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease and neural tube defects. Vitamin B6 may be included in the form of pyridoxine hydrochloride.

Vitamin B9 can prevent neural tube defects such as spina bifida caused by disturbed homocysteine metabolism. Vitamin B9 also is important for the formation of red and white blood cells within bone marrow and plays a role in heme formation. Further, folate deficiencies inhibit the activity of vitamin B1. Vitamin B9 may be included in the form of folic acid. In another embodiment, vitamin B9 may be included in the forms of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof. 100% RDA for children 6-59 months old is 0.15 mg/day. 50% RDA for an adult female is 0.2 mg/day. A useful form of vitamin B9 for the disclosed formulations is folic acid.

Vitamin B12 can be converted to the active coenzymes, methylcobalamin and 5'-deoxyadenosylcobalamin. These coenzymes are necessary for folic acid metabolism, conversion of coenzyme A and myelin synthesis. Methylcobalamin also catalyzes the demethylation of a folate cofactor, which is involved in DNA synthesis. A lack of demethylation may result in folic acid deficiency. Deoxyadenosylcobalamin is the coenzyme for the conversion of methylmalonyl-CoA to succinyl-CoA, which plays a role in the citric acid cycle. Cobalamin, along with pyridoxine and folic acid, also are implicated in the proper metabolism of homocysteine, a breakdown product of the amino acid methionine, which is correlated with an increased risk of heart disease due to its negative effects on endothelial function. Vitamin B12 may be included in the form of cyanocobalamin. 100% RDA for children 6-59 months old is 0.0009 mg/day. 50% RDA for an adult female is 0.0012 mg/day. Useful forms of vitamin B12 for the disclosed formulations include cyanocobalamin and methylcobalamin.

Vitamin C is a co-substrate in metal catalyzed hydroxylations. Like beta-carotene, vitamin C has antioxidant properties. It interacts directly with superoxide hydroxyl radicals and singlet oxygen, and also provides antioxidant protection for folate and vitamin E, keeping vitamin E in its most potent form. Vitamin C may afford protective effects against preeclampsia by participating in the scavenging of free radicals. Indeed, significantly lower levels of vitamin C have been observed in preeclamptic women than in controls.

Vitamin C also enhances the absorption of iron. In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. Vitamin C may be included in the form of ascorbic acid. 100% RDA for children 6-59 months old is 30 mg/day. 50%

RDA for an adult female is 37.5 mg/day. Useful forms of vitamin C for the disclosed formulations include ascorbic acid and sodium ascorbate.

Vitamin D3 is a fat-soluble "hormone like" substance important for the maintenance of healthy bones. This vitamin increases the absorption of calcium and phosphorous from the gastrointestinal tract, and improves mineral resorption into bone tissue. Vitamin D can be converted to its active form from exposure of the skin to sunlight. Deficiencies in vitamin D3 can lead to increased bone turnover and loss, and when severe, osteomalacia, or softening of the bones. Supplementation with vitamin D3 has been shown to moderately reduce bone loss, increase serum 25-hydroxyvitamin D, and decrease serum parathyroid hormone levels. Vitamin D3 also plays a role in the maintenance of calcium and phosphorus homeostasis, but it is also active in cell differentiation and immune function. Vitamin D3 may be included in the form of cholecalciferol. 100% RDA for children 6-59 months old is 0.005 mg/day. 50% RDA for an adult female is 0.0075 mg/day. Useful forms of vitamin D for the disclosed formulations include cholecalciferol and ergocalciferol.

Vitamin E is a fat-soluble vitamin antioxidant found in biological membranes where it protects the phospholipid membrane from oxidative stress. Vitamin E inhibits the oxidation of unsaturated fatty acids by trapping peroxyl free radicals. It is also an antiatherogenic agent, and studies have demonstrated a reduced risk of coronary heart disease with increased intake of vitamin E. In addition, vitamin E, like beta-carotene and vitamin C, may afford protective effects against preeclampsia by participating in the scavenging of free radicals. As with vitamin C, significantly lower levels of vitamin E have been observed in preeclamptic women than in controls. Vitamin E may be included in the form of d-alpha-tocopheryl acetate or d-alpha tocopheryl succinate.

Iron is necessary to carry oxygen to bodily tissues via the hemoglobin part of red blood cells. Supplemental intake of iron is critical to preventing anemia, a disorder associated with a variety of physiological states including, for example, pregnancy or high parasite infestation. The formulations may include iron in either chelated or nonchelated form. Iron may be included in the form of a polysaccharide iron complex. In another specific embodiment, iron may be included in the form of an equivalent molar amount of ferrous fumarate. 100% RDA for children 6-59 months old is 10 mg/day. 50% RDA for an adult female is 9 mg/day. Useful forms of iron for the disclosed formulations include NaFeEDTA, ferrous sulfate, ferrous gluconate, ferrous fumarate, and ferric pyrophosphate.

Magnesium is found primarily in both bone and muscle and is important for over 300 different enzyme reactions. A primary function of magnesium is to bind to phosphate groups in adenosine triphosphate (ATP), thereby forming a complex that assists in the transfer of ATP phosphate. Magnesium also functions within cells as a membrane stabilizer. Magnesium plays roles in nucleic acid synthesis, glycolysis, transcription of DNA and RNA, amino acid activation, membrane transport, transketolase reactions, and protein synthesis. It is also involved in the formation of cAMP, a cytosolic second messenger that plays a role in cell signaling mechanisms. Magnesium also functions both synergistically and antagonistically with calcium in neuromuscular transmission. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Indeed, oral magnesium therapy improves endothelial function in patients with coronary disease.

Magnesium is available in a variety of salts and can be included in the formulations in either chelated or nonchelated form. In one embodiment, magnesium is included in the form of magnesium oxide.

Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zinc stabilizes RNA and DNA structures, forms zinc fingers in nuclear receptors, and is a component of chromatin proteins involved in transcription and replication. Deficiencies of zinc during pregnancy have been shown to contribute to severe fetal abnormalities. Zinc is available in many forms and may be included in the formulations in chelated or nonchelated form. In one embodiment, zinc may be included in the form of zinc oxide. 100% RDA for children 6-59 months old is 4.1 mg/day. 50% RDA for an adult female is 8 mg/day. Useful forms of zinc for the disclosed formulations include zinc acetate, zinc gluconate, zinc picolinate, and zinc sulfate.

Selenium is an essential micronutrient for animals. Selenium is a component of the amino acids selenocysteine and selenomethionine. Selenium functions as cofactor for reduction of antioxidant enzymes, such as glutathione peroxidases and certain forms of thioredoxin reductase. The glutathione peroxidase family of enzymes (GSH-Px) catalyzes certain reactions that remove reactive oxygen species such as hydrogen peroxide and organic hydroperoxides.

Selenium also plays a role in the functioning of the thyroid gland and in every cell that uses thyroid hormone, by participating as a cofactor for the three of the four known types of thyroid hormone deiodinases, which activate and then deactivate various thyroid hormones and their metabolites: the iodothyronine deiodinases are the subfamily of deiodinase enzymes that use selenium as the otherwise rare amino acid selenocysteine. Selenium may inhibit Hashimoto's disease, in which the body's own thyroid cells are attacked as alien.

Manganese is an essential trace nutrient. The classes of enzymes that have manganese cofactors are very broad, and include oxidoreductases, transferases, hydrolases, lyases, isomerases, ligases, lectins, and integrins.

Copper is an essential trace element in animals. Because of its role in facilitating iron uptake, copper deficiency can produce anemia-like symptoms, neutropenia, bone abnormalities, hypopigmentation, impaired growth, increased incidence of infections, osteoporosis, hyperthyroidism, and abnormalities in glucose and cholesterol metabolism.

Cobalt is an essential trace element. It is a key constituent of cobalamin, also known as vitamin B12, which is the primary biological reservoir of cobalt as an "ultratrace" element. The cobalamin-based proteins use corrin to hold the cobalt. Coenzyme B12 features a reactive C—Co bond, which participates in its reactions. In humans, B12 exists with two types of alkyl ligand: methyl and adenosyl. MeB12 promotes methyl (—CH3) group transfers. The adenosyl version of B12 catalyzes rearrangements in which a hydrogen atom is directly transferred between two adjacent atoms with concomitant exchange of the second substituent, X, which may be a carbon atom with substituents, an oxygen atom of an alcohol, or an amine. Methylmalonyl coenzyme A mutase (MUT) converts MM1-CoA to Su-CoA, an important step in the extraction of energy from proteins and fats.

Iodine's main role in animal biology is as a constituent of the thyroid hormones thyroxine (T4) and triiodothyronine. These are made from addition condensation products of the amino acid tyrosine, and are stored prior to release in an iodine-containing protein called thyroglobulin. T4 and T3 contain four and three atoms of iodine per molecule, respectively. The thyroid gland actively absorbs iodide from the blood to make and release these hormones into the blood, actions that are regulated by a second hormone. Thyroid hormones play a basic role in biology, acting on gene transcription to regulate the basal metabolic rate. The total deficiency of thyroid hormones can reduce basal metabolic rate up to 50%, while in excessive production of thyroid hormones the basal metabolic rate can be increased by 100%.

Iodine has a nutritional relationship with selenium. A family of selenium-dependent enzymes called deiodinases converts T4 to T3 (the active hormone) by removing an iodine atom from the outer tyrosine ring. These enzymes also convert T4 to reverse T3 (rT3) by removing an inner ring iodine atom, and convert T3 to 3,3'-diiodothyronine (T2) also by removing an inner ring atom. It is also important for fetal and neonatal development. 100% RDA for children 6-59 months old is 0.09 mg/day. 50% RDA for an adult female is 0.075 mg/day. Useful forms of iodine for the disclosed formulations include potassium iodide and potassium iodate.

Other therapeutic, nutritional, prophylactic or diagnostic agents can also be included. In one embodiment, antiparasitic agents are incorporated into the particles. Antiparasitic agents, such as anti-protozoa agents, antihelminthics, and combinations thereof, include, but are not limited to, antinematodes, anticestodes, antitrematodes, antiamoebics, antiprotozoals, and combinations thereof.

Suitable antinematodal drugs include, but are not limited to, benzimidazoles (e.g., mebendazole, thiabendazole), avermectins (e.g., ivermectin), pyrantel pamoate, diethylcarbamazine, and combinations thereof.

Suitable anticestodes include, but are not limited to, niclosamine, praziquantel, albendazole, and combinations thereof.

Suitable antitrematodes include, but are not limited to, praziquantel.

Suitable antiamoebics include, but are not limited to, rifampin, amphotericin B, and combinations thereof.

Suitable antiprotozoals include, but are not limited to, melarsoprol, eflornithine, metronidazole, tinidazole, miltefosine, and combinations thereof.

The particles can contain one or more antiviral and/or antimicrobial agents. Suitable agents include anti-influenza agents, anti-poliovirus agents, antihepatitis agents, anti-arboroviral agents (anthropod-born viruses such as dengue fever, yellow fever, and malaria), anti-rotavirus agents, anti-Ebola virus agents, anti-Marburg virus agents, anti-Lassa virus agents, and combinations thereof. Suitable antimicrobial agents include, but are not limited to, anti-cholera agents, anti $E$-coli agents, anti-tuberculosis agents, anti-leprosy agents, and combinations thereof.

Different agents, and different combinations of agents, can be combined in the same particle, different particles, or combinations thereof. This can be done for reason of convenience, such as having separate particles for different agents for convenience in combining or mixing different agents in different formulations, or in order to increase or optimize the stability or form of the agents based on the composition of the particle.

Different agents, and different combinations of agents, can be dispersed in the same matrix particles, different matrix particles, or combinations thereof. This can be done for reason of convenience, such as having separate matrix particles for different agents for convenience in combining or mixing different agents in different formulations, or in order to increase or optimize the stability or form of the agents based on the composition of the particle.

The agents should be stable to conditions encountered during storage, food preparation, and/or cooking.

B. Matrix Materials

The particles are dispersed in a matrix that can include stabilizing materials such as sugars and oils, hydrogel, or combinations thereof.

Stabilizing Sugars/Oils

The particles can be dispersed into a matrix formed of one or more stabilizing materials, such as sugars and/or oils. In one embodiment, the matrix is formed from one or more sugars which stabilize the materials forming the particles. Exemplary sugars include, but are not limited to, sucrose, trehalose, and carbohydrates such as plant components.

Hydrogels

The matrix for the micronutrients can be formed of a hydrogel, which is then encapsulated with salt for formulation and delivery. There are a number of biocompatible and GRAS (generally regarded as safe by the Food and Drug Administration). The examples demonstrate formulation using hyaluronic acid. Other natural polymers include cyclodextrin, collagen, alginate, gelatin and chitin. Synthetic polymers that form hydrogels include polyethylene glycol and copolymers thereof, ethylene glycol dimethacrylate, hydroxyethyl methacrylate, poly(butylene oxide), polycaprolacton, poly(ethylene oxide) and copolymers thereof, poly(ethylene imine, poly(ethyl methacrylate), propylene fumarate, poly(hydroxy butyrate), poly(hydroxyethyl methacrylate), poly(hydroxypropyl methacrylamide), poly(lactic acid), poly(lactic-co-glycolic acid), poly(N-vinyl pyrrolidone), poly(propylene oxide, poly(vinyl alcohol), poly(vinyl acetate), and poly(vinyl amine). Any material can be used to form the matrix provided it can be coated with the polymer coating or jacket.

Polymers are selected for compatibility with processing conditions and stability requirements, and may require some chemical modifications to increase stability under the conditions to be used. These materials can be used in their pure (non-gel) polymer form, modified and unmodified, or in their gel form. Criteria for selection include 1) improved stability of micronutrients from the environment (e.g. moisture, storage, cooking, etc.), 2) protecting micronutrients from other chemically reactive species and 3) quick (<1 hr) release in gastric fluid/stomach.

In the preferred embodiment, the matrix is made of a hyaluronic acid derivative, as shown below.

Scheme 1. HA derivatives synthesis

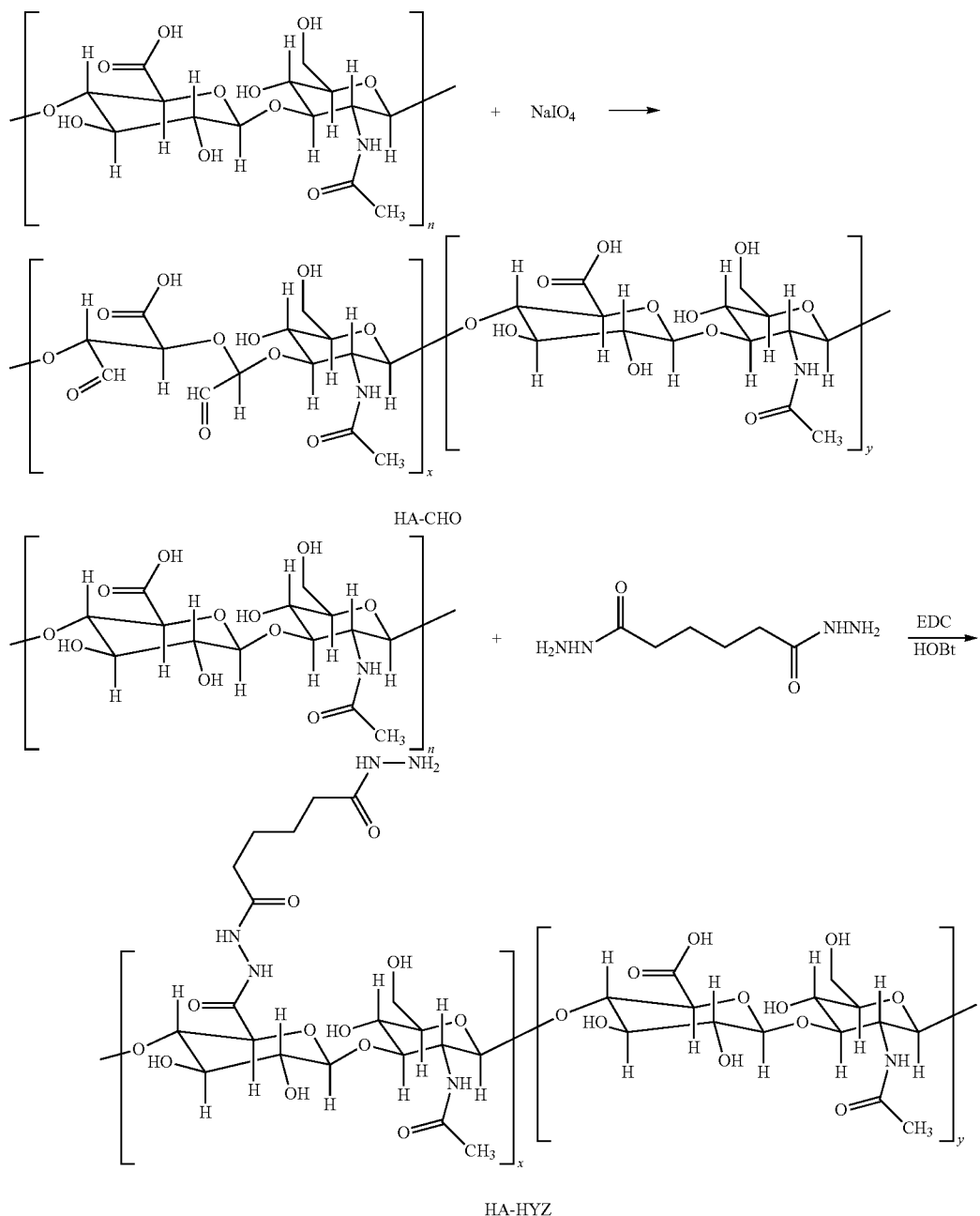

C. pH-Sensitive, Thermally Stable Polymers

The matrix is coated or encapsulated with one or more pH-sensitive, thermally stable biocompatible polymers. The solubility of the polymer is pH-dependent such that a desired release point can be achieved by selecting the appropriate polymer. For example, if release is desired in the stomach, the pH-sensitive polymer ideally dissolves at a pH less than 3, preferably less than 2, such as 1-2. In other embodiments, release may be desired in the small intestine, wherein the polymer dissolves at the higher pH of the duodenum (pH 6-6.5) or the small intestine, such as 6-8, more preferably 7-8. For agricultural applications, such as mineral supplements to ruminants like cattle, sheep and goats, pH release between 5 and 6 is desirable to achieve release within the rumen.

The polymer is also thermally stable. "Thermally stable", as used herein, means that at a given temperature, the polymer coating does not degrade and allow leakage of the materials from the core. Preferred polymers are thermally stable during cooking, so that the formulation can be added to food like regular salt. Typically, food is prepared by boiling or simmering for 10 minutes to hours, cooking in a pot or pan over a fire, or baking in an oven for 15 minutes to an hour. The formulations will typically be designed for the most common cooking conditions in the geographic region in which the salt formulation is to be distributed.

The polymer is preferably water-insoluble so that the polymer coating does not dissolve when in contact with moisture or water or an aqueous solution, such as during storage or cooking. The polymer coating should remain sufficiently intact, e.g., up to or at least about one hour, such that the encapsulated agents are not released and/or denatured. The polymer is sufficiently non-porous such that water or other aqueous media cannot diffuse through the polymer and dissolve the materials in the core. The non-porosity may also serve to stabilize the materials in the core by preventing oxidation of air-sensitive materials. The material should remain non-porous under storage conditions for a period of weeks to months and for at least about 20 minutes to about 4 hours, preferably for at least about 20 minutes to about 2 hours, more for at least about 20 minutes to about 1 hour under food preparation and/or cooking conditions.

Exemplary polymers include polymethacrylates sold under the tradename EUDRAGIT®, naturally occurring cellulosic polymers (e.g., cellulose acetate succinate, hydroxy propyl methyl cellulose phthalate, and hydroxy propyl methyl cellulose acetate succinate) and other polysaccharides (e.g., sodium alignate, pectin, chitosan) or semi-synthetic or synthetic derivatives thereof, poly(2-vinylpyridine-co-styrene), polyvinyl acetate phthalate, shellac, fatty acids (e.g., stearic acid), waxes, plastics, and plant fibers.

In some embodiments, the one or more polymers is a EUDRAGIT®. In some embodiments, the EUDRAGIT® dissolves at a pH less than 6, preferably less than 5, 4, or 3, such as 1-3, or 1-2. Such polymers typically have functional groups, which are protonated at low pH, such as amines, which increase the solubility in aqueous media due to the formation of charged groups. Examples of such polymers include, but are not limited to, EUDRAGIT® E PO (dimethylaminoethyl methacrylate, butyl methacrylate, and methyl methacrylate (2:1:1 ratio); "EPO"), chitosan, polymers which are cationic or become cationic under certain conditions (e.g., in vivo). The structure of EUDRAGIT® E PO is shown below:

Scheme 2

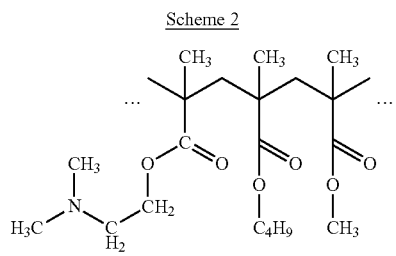

In other embodiments, the polymer is an enteric polymer which dissolves at a pH greater than the pH of the stomach, such as greater than pH 5-6. Such polymers typically have functional groups that form salts (e.g., carboxylic acids) at higher pH in order to increase solubility. In some embodiments, the polymer dissolves at a pH greater than about 5.5, such as EUDRAGIT® L 30 D-55 and L 100-55; greater than about 6.0, such as EUDRAGIT® L 100 and L 12.5; and greater than about 7.0, such as EUDRAGIT® S 100, S 12.5, and FS 30 D.

The thickness of the polymer coating or encapsulate can be varied in order to achieve the desires release rate. In some embodiments, the thickness of the coating is from about 1 Angstrom to hundreds of microns. In some embodiments, the thickness of the coating is from about 5 to about 200 microns, preferably from about 10 to about 100 microns, more preferably from about 10 microns to about 75 microns, most preferably from about 20 microns to about 50 microns.

In some embodiments, the micronutrient particles can be dispersed in the pH-sensitive polymer coating as well as in the matrix.

D. Salt Coatings and Other Coatings

The polymer coated matrix containing particles can be coated with salt, sugar, or other coating material, preferably salt. In the preferred embodiment, the salt is one or more salts that are suitable for consumption by an animal, such as a human. Exemplary salts include, but are not limited to, sodium and/or potassium chloride, magnesium chloride, potassium iodide, phosphates, and combinations thereof. In some embodiments, the thickness of the coating is from about 1 Angstrom to hundreds of microns. In some embodiments, the thickness of the coating is from about 5 to about 200 microns, preferably from about 10 to about 100 microns, more preferably from about 10 microns to about 75 microns, most preferably from about 20 microns to about 50 microns. Salts may be purified or impure, such as salt obtained by evaporation of salt or brackish water. The concentration of the salt can be from about 10% to about 80% by weight of the particle, preferably from about 10% to about 70%, more preferably from about 20% to about 60%, most preferably from about 40% to about 60%.

Other coating materials include sugar and other food components suitable as a coating. Preferred coating material can be compatible with and/or can help make the formulations compatible with food and products and components to be included in food (such as during food preparation or cooking).

To coat the polymer matrix with salts, sugar, or other coating material, compositions serving as binders may be used to facilitate coating. The binders are used to bind the salt crystals to each other and to the surface of the polymer matrix. Exemplary compositions used as binders include, but are not limited to, wheat starch, corn starch, potato starch, polyvinyl alcohol (PVA), carboxymethyl cellulose, and methyl cellulose.

III. Methods of Making

A. Preparation of Particles

The particles can be prepared using techniques known in the art. The mixture of vitamins and minerals, and any other agents, are processed with one or more stabilizing materials to form particles using a suitable technique such as crystallization, emulsion-based techniques, spray drying, and flash drying. The activity and stability of the particles can be evaluated using techniques known in the art such as ELISA, colorimetric assay, elemental analysis, mass spectroscopy, and/or HPLC. Combinatorial nutrient encapsulation studies can be conducted to determine if any of the agents in the particle react adversely with each other. If such adverse reactions are observed, one or more of the agents in the particles can be coated or otherwise treated to reduce or prevent adverse reactions. The particles can have an average diameter from about a few microns to about 200 microns.

B. Polymer Encapsulation of Particles

The particle matrix is encapsulated in the pH-responsive polymer using techniques known in the art. Suitable techniques include, but are not limited to, dipping, coating, emulsion-based encapsulation techniques, spray drying, and fluidized bed. The release kinetics of the agents in the particles is dependent on a variety of factors, such as pH at which the polymer dissolved and coating thickness. In some embodiments, the thickness of the coating is from about 1 Angstrom to hundreds of microns. In some embodiments, the thickness of the coating is from about 5 to about 200 microns, preferably from about 10 to about 100 microns, more preferably from about 10 microns to about 75 microns, most preferably from about 20 microns to about 50 microns.

C. Salt Coating

The polymer-encapsulated particles can be coated with one or more salts (or other coating material) using techniques known in the art. A preferred method uses a fluidized bed. Other suitable techniques include crystallization of the salt on the polymer jacket and wet and dry salt fabrication techniques. The diameter of the final salt-coated particles can vary but it typically from about 500 microns to about 1000 microns (1 mm).

IV. Methods of Use

The formulations, such as fortified salt formulations, can be packaged and distributed for use during food preparation and cooking. The formulations may be used without salt coating (or other coatings) to fortify flour and other foods. The coating material used can be selected based on the food in which the formulation is used. Also, the formulations can withstand liquid and solid sterilization, which is useful for beverage, liquid food, or solid food preparation.

The formulations described herein can be used to treat or prevent malnutrition and/or micronutrient deficiency, particularly in populations susceptible to such maladies, such as children and adults in developing countries and countries suffering from severe drought. The formulations described herein can be incorporated in food vehicles for use by the populations in need. Because of high variability in commonly consumed food vehicles by the populations in need, the disclosed formulations can be used with and incorporated into a variety of food vehicles, including wheat flour, cooking oil, sugar, and salt.

In some embodiments, the particles contain the essential micronutrients vitamins A, B1, B2, B3, B6, B7, B9, B12, C, D, and E; molybdenum, chromium, selenium, iodine, copper, manganese, zinc, and iron. The amount of the micronutrients incorporated into the particles can be based on the RDA for a particular micronutrient. For example, the amount of micronutrients can be based on 50%, 60%, 70%, 80%, 90%, or 100% RDA.

In some embodiments, the formulation is used for universal fortification where the target population is the general population including healthy individuals. The formulation contains 100% RDA for iodine and less than or equal to 50% RDA for all other micronutrients. In other embodiments, the formulation is used for targeted fortification where the target population is micronutrient deficient households. The formulation can contain, for example, 100% RDA for children 6-59 months old.

In particular embodiments, 2 g/day of the formulation can provide 100% RDA for children for the micronutrients iodine (0.09 mg/day), zinc (4.1 mg/day), folic acid (0.15 mg/day), vitamin B12 (0.0009 mg/day), vitamin A (0.4 mg/day), vitamin C (30 mg/day), vitamin D (0.005 mg/day), and iron (10 mg/day).

In other embodiments, 5 g/day of the formulation can provide 50% RDA for adult woman for the micronutrients iodine (0.075 mg/day), zinc (8 mg/day), folic acid (0.2 mg/day), vitamin B12 (0.0012 mg/day), vitamin A (0.45 mg/day), vitamin C (37.5 mg/day), vitamin D (0.0075 mg/day), and iron (9 mg/day).

The data in the examples show that formulations containing B9 and B12 exhibited no release in water at room temperature or 100° C. However, in simulated gastric fluid (SGF), the formulations released all of the B9 and B12 within about one hour. ELISA showed that B9 and B12 were stable in the formulations described herein and were not degraded or denatured.

In other embodiments, the formulations can be used in a variety of foods and staples. For example, the formulations can constitute or be included in food ingredients such as salt, sugar, oil, flour, baking soda, baking powder, corn starch, butter, shortening, meal (such as corn or other grain meal), coffee, tea, spices, flavorings, extracts, etc. Examples of foods in which the formulations can be incorporated include beverages, such as milk, water, soda and other carbonated beverages, sports drinks, juice, baked goods such as breads, cakes, cookies, and pies, processed foods such as yogurt, cheese, and nutrition or energy bars.

In other embodiments, the formulations are used for agricultural purposes. Minerals and salt are essential for animal health, and it is difficult for these formulations to maintain integrity under adverse climatic conditions and in storage. These formulations are weather resistant and stable in storage in heat and high humidity. Advantages to the pH-dependent release are that formulations can be designed to provide maximum release in the region of the gastrointestinal tract where uptake is most effective, such as the rumen. Additional benefits are obtained through the incorporation of vitamins and medicines such as deworming agents which otherwise would have to be administered separately.

The present invention will be further understood by reference to the following non-limiting examples.

EXAMPLES

Example 1

Polymer Solubility Studies

Methods and Materials

The solubility of the commercially available polymer dimethylaminoethyl methacrylate, butyl methacrylate, and methyl methacrylate (2:1:1 ratio) (EUDRAGIT® E PO ("EPO")) at pH from 1-12 was evaluated. 10 mg/ml of the polymer was added to solutions having a pH of 1 2, 4, 7.4, 10, and 12 and observed over 8 hours.

EUDRAGIT® E PO was dissolved in simulated gastric fluid (SGF) at 37° C. at various concentrations over 2.5 hours to determine the solubility limit in simulated gastric fluid.

Results

Figure 2:
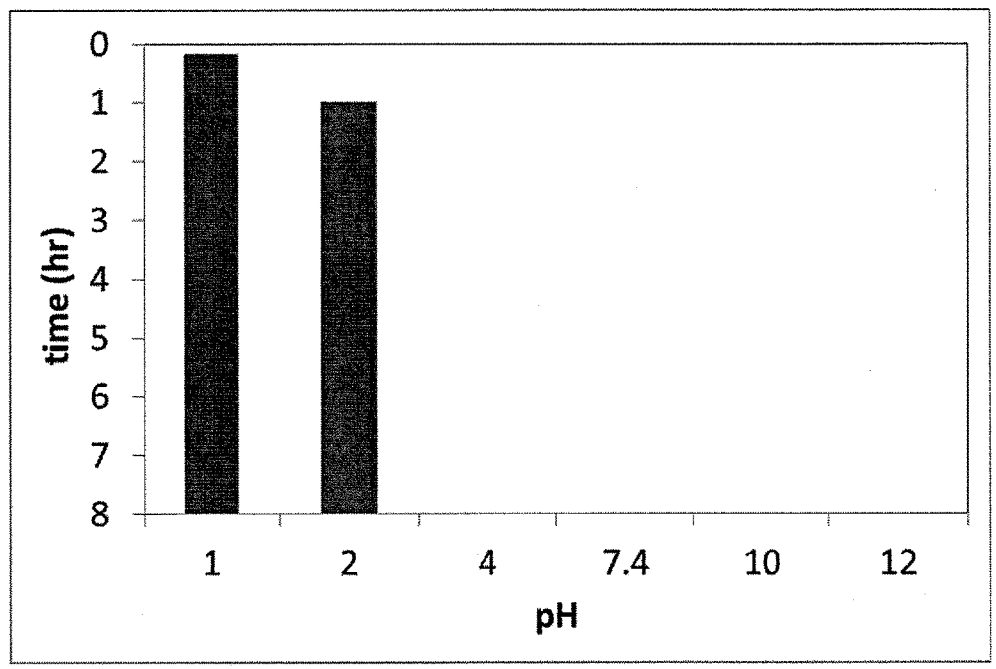
FIG. 2 is a graph showing the solubility of 10 mg/ml of EUDRAGIT® E PO ("EPO") as a function of pH at 37° C. over an eight-hour period.

The pH-dependent solubility is shown in FIG. 2. In a two-hour period, the polymer is dissolved at pH 2 and below. The polymer was insoluble at pH 4, 7.4, 10, and 12.

Figure 3:
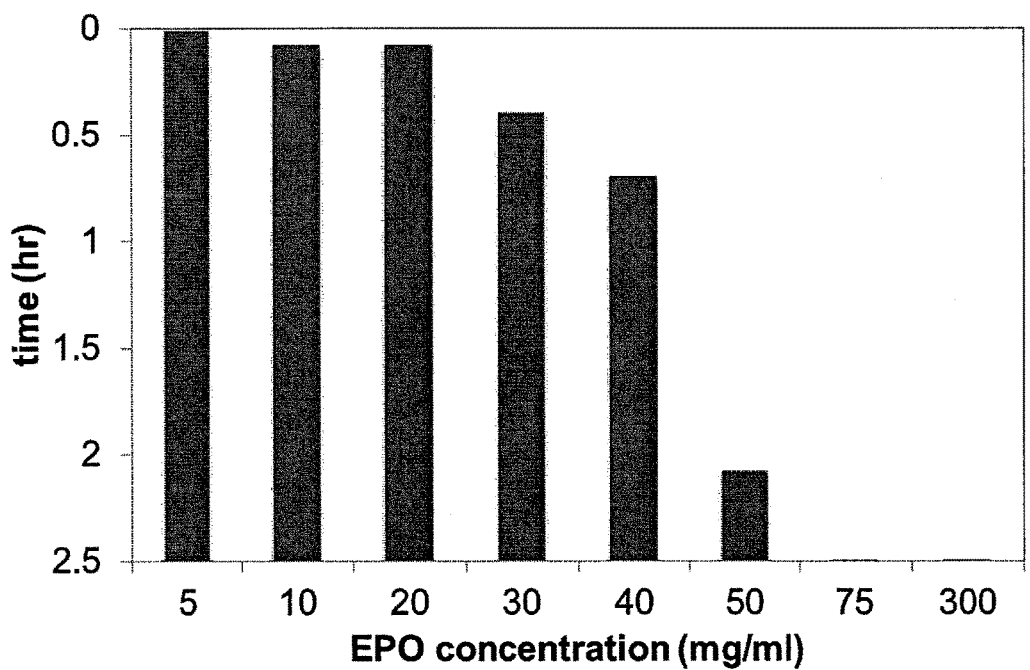
FIG. 3 is a graph showing the solubility of EUDRAGIT® E PO in simulated gastric fluid (pH 1.2) at 37° C. over 2.5 hours.

The dissolution in simulated gastric fluid ("SGF") is shown in FIG. 3. EPO has a maximum solubility of 50 mg/mL. Given the volume of the stomach is 20-100 mL, 1-5 g of EPO can be delivered to the stomach and still retain full dissolution.

Example 2

Dye Release Studies of Crystallized Dye/Sugar Mixtures Coated with EUDRAGIT® E PO Materials and Methods 0.6 mL of a sugar/dye solution (0.5 M trehalose+sucrose) was crystallized in a beaker. The crystallized mixture was coated with 1 mL of a EUDRAGIT® E PO ("EPO") solution in acetone (1%, 5%, 10%, and 20%). The EPO film thickness was imaged and measured.

The release kinetics were studied in water and SGF (release volume of 4 mL) over a period of two hours. Time points were taken at 10 min, 1 hr, and 2 hr, and the dye release was quantified by absorbance measurement at 628 nm.

Using the 5% EPO coating, the release was tested at different temperatures.

Results

Figure 4:
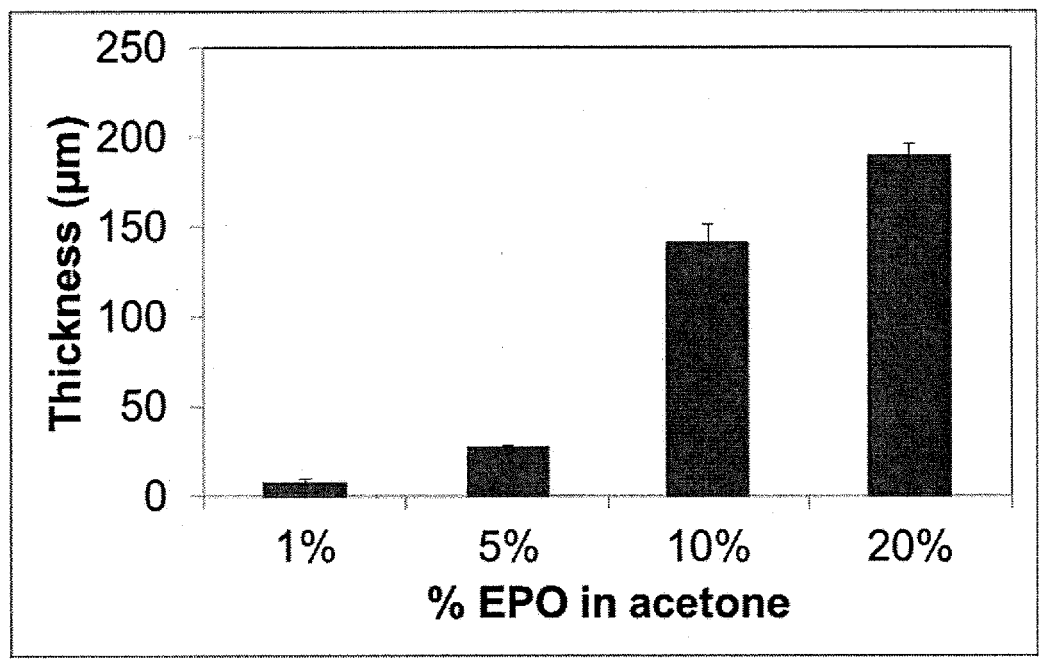
FIG. 4 is a graph showing the coating thickness of EUDRAGIT® E PO (microns) as a function of EUDRAGIT® E PO concentration in the coating solution.
Figure 5A:
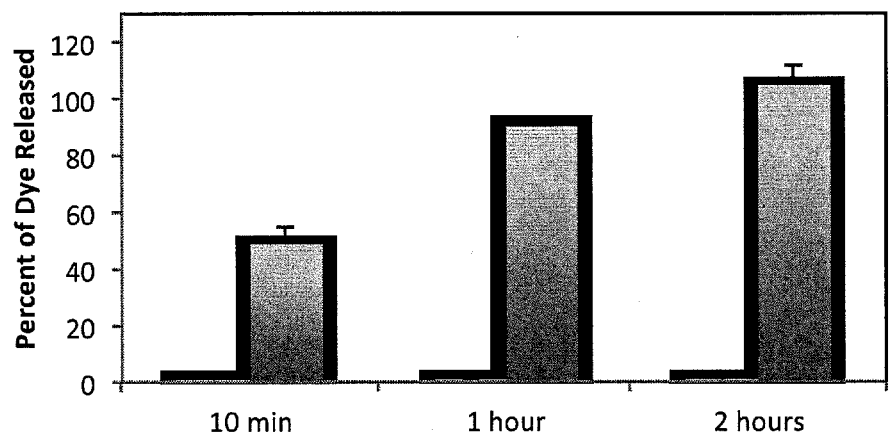
FIGS. 5A-D are graphs showing dye release (percent released) at 25° C. in water and simulated gastric fluid for 1% EUDRAGIT® E PO coating (FIG. 5A), 5% EUDRAGIT® E PO coating (FIG. 5B), 10% EUDRAGIT® E PO coating (FIG. 5C), and 20% EUDRAGIT® E PO coating (FIG. 5D).
Figure 5B:
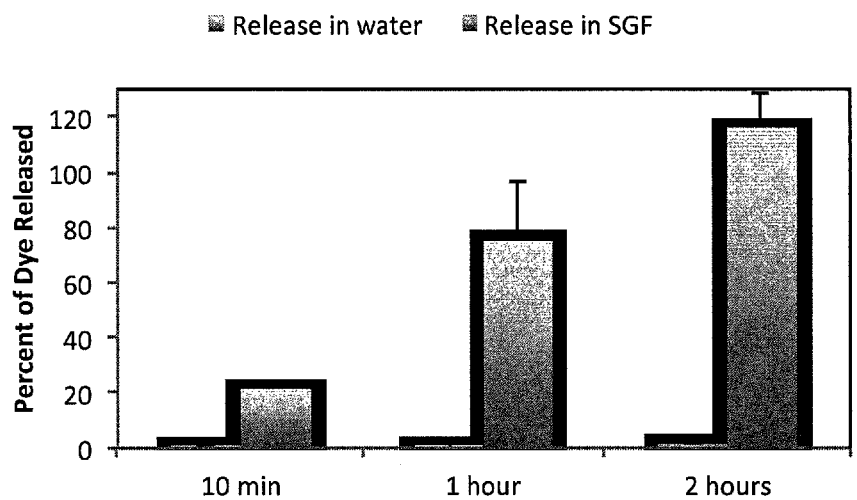
Figure 5C:
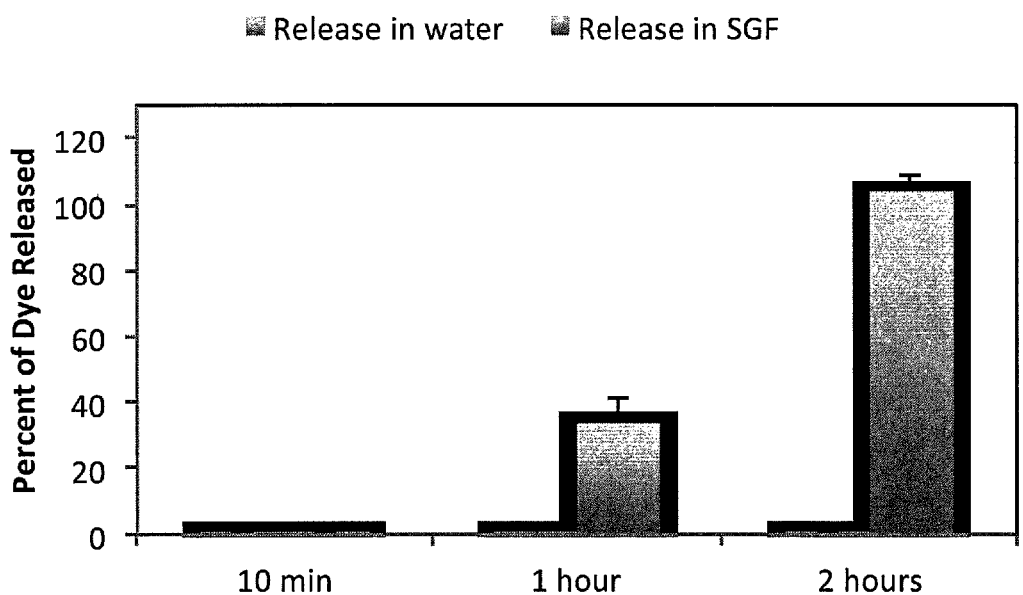
Figure 5D:
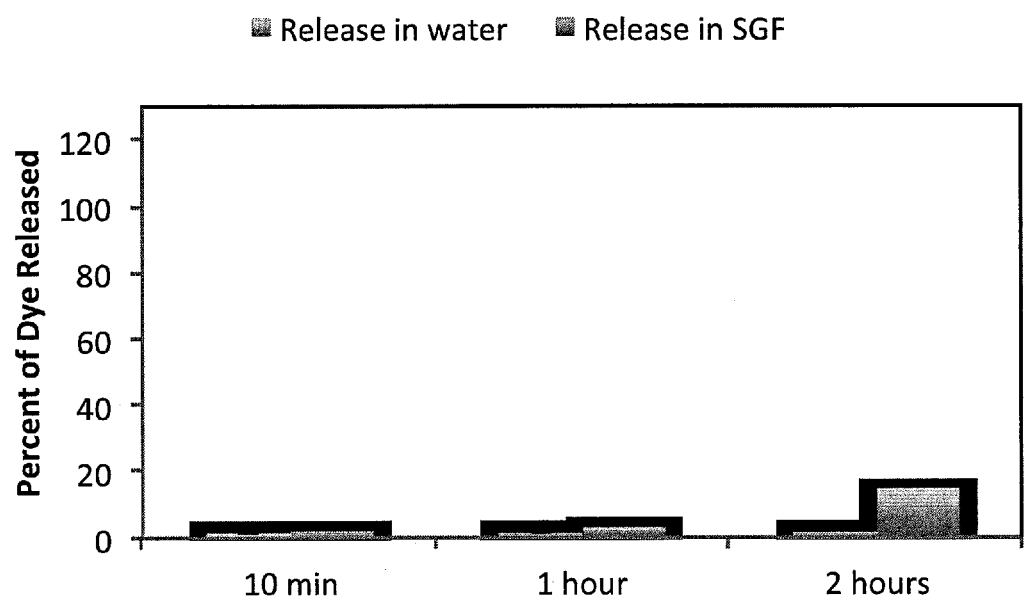

The film thickness results are shown in FIG. 4. At 1% EPO, the coating thickness was about 5 microns while at 20% EPO, the coating thickness was about 200 microns. Varying the concentration of the polymer varies the coating thickness. Any volatile organic solvents can be used to dissolve the polymer. Representative polymer solvents include organic solvents such as chloroform, dichloromethane, tetrafluoroethylene, and acyl acetate.

The release kinetic results are shown in FIG. 5. In water, there was negligible dye release, and in SGF, the speed of dye release correlated with the thickness.

Figure 6A:
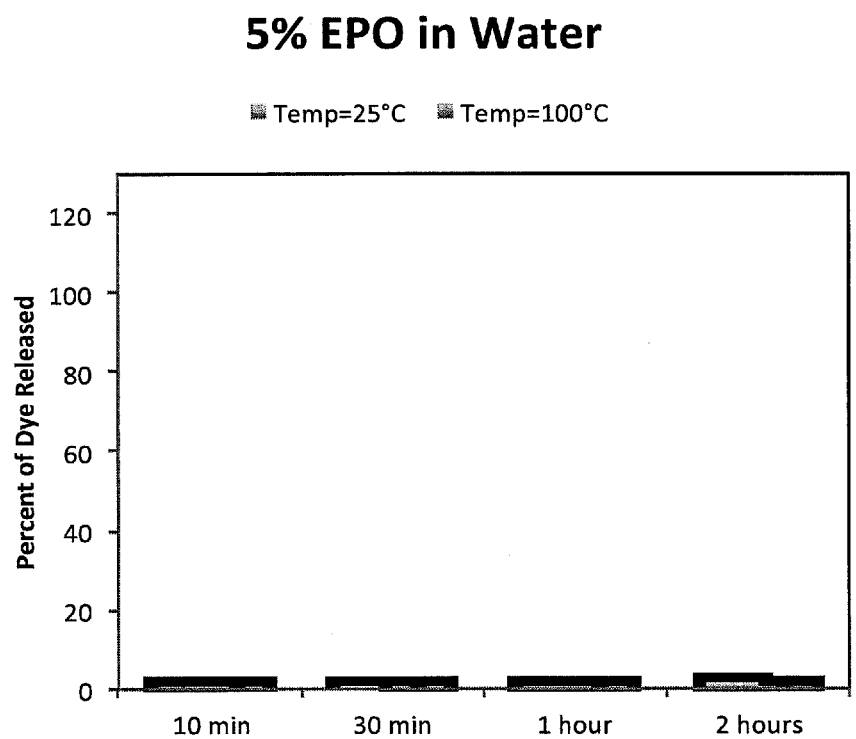
FIGS. 6A and 6B are graphs showing the release of a blue dye into water (FIG. 6A) and simulated gastric fluid (FIG. 6B) for 5% EUDRAGIT® E PO coating at 25° C. and 37° C.
Figure 6B:
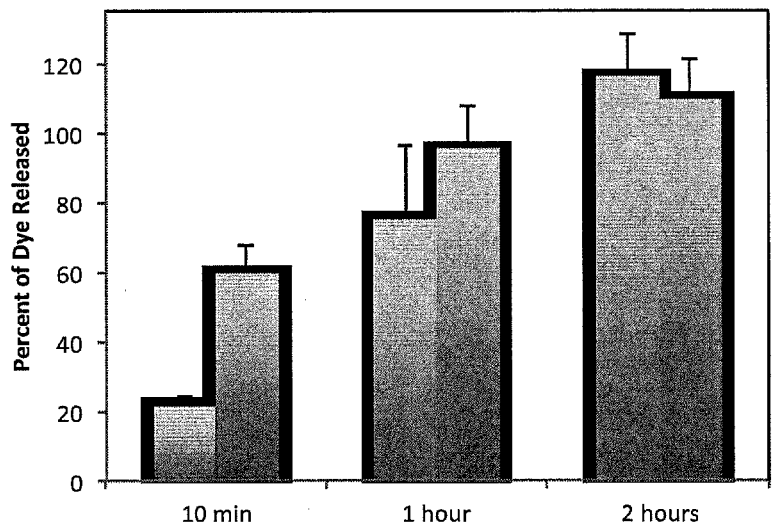

The temperature release results are shown in FIGS. 6A and 6B. Negligible dye was released into water at 100° C. (FIG. 6A). The dye released faster in SGF at 37° C., which is the physiologically relevant condition (FIG. 6B).

Example 3

Release Studies of EUDRAGIT® E PO-Coated Micronutrients

Materials and Methods 0.6 mL of nutrient/sugar solutions (1:1 ratio) were crystallized and coated with a 5% (by weight) solution of EUDRAGIT® E PO ("EPO") in acetone.

To mimic food preparation then ingestion, the samples were submerged in 4 mL water (at 25° C. or 100° C.) for one hour and transferred to 4 mL simulated gastric fluid at 37° C. for two hours. Aliquots were taken at 1, 2, and 3 hours, and the release was quantified using ELISA.

Results

Figure 7A:
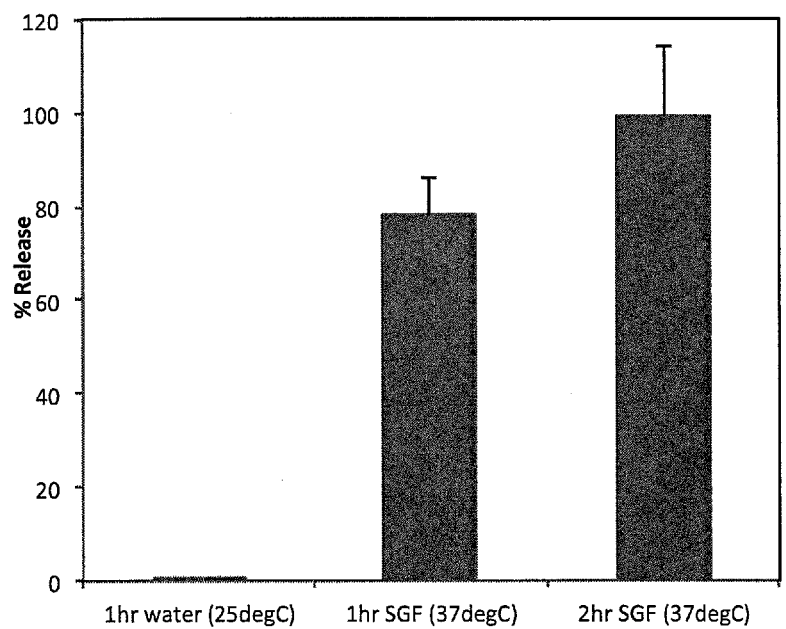
FIGS. 7A and 7B show the release of B9 (percent release) in water (FIG. 7A) and simulated gastric resistant fluid (FIG. 7B) as a function of temperature.
Figure 7B:
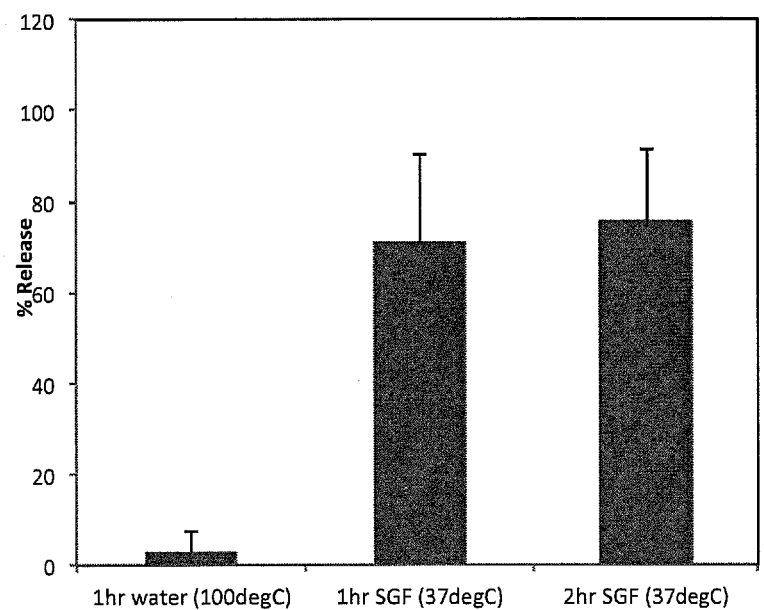
Figure 8A:
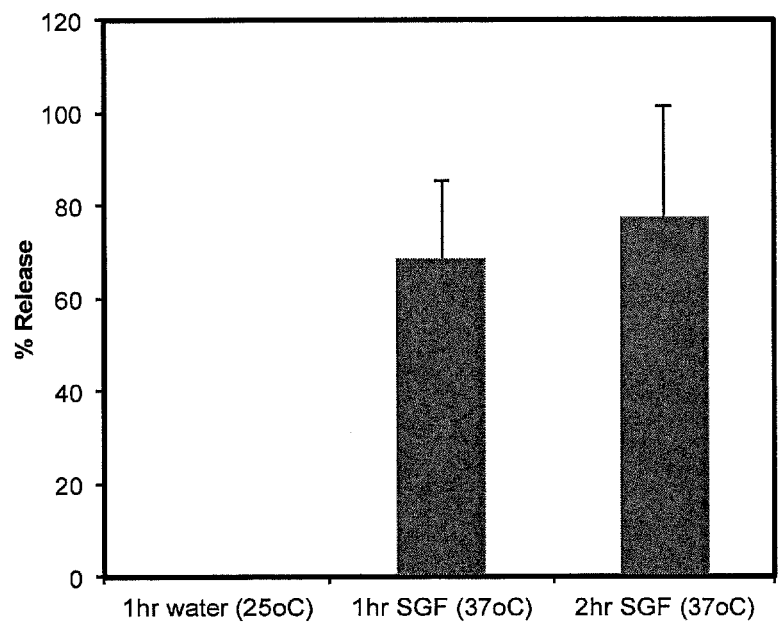
FIGS. 8A and 8B show the release of B12 (percent release) in water (FIG. 8A) and simulated gastric resistant fluid (FIG. 8B) as a function of temperature.
Figure 8B:
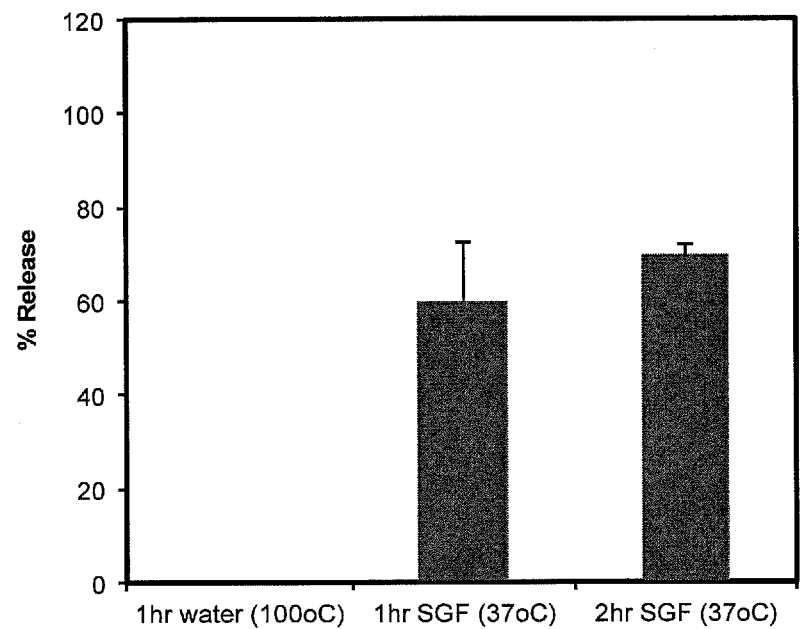

The results are shown in FIGS. 7A and 8A (one hour at room temperature, then body temperature) and 7B and 8B (one hour at boiling water temperature, then body temperature). For Vitamin B9 (FIGS. 7A and 7B) and B12 (FIGS. 8A and 8B), there was negligible release in water at both 25° C. and 100° C. and near complete release after one hour in SGF.

Example 4

Encapsulation of Micronutrients in a Hydrogel

Materials and Methods

Preparation of HA HGPs: The HGPs were formulated by an inverse emulsion crosslinking method according to Jha et al., *Biomaterials*, 30:6964 (2009). Both the crosslinking density and the size of the HGPs were modulated systematically. The formulated HGPs were characterized by scanning electron microscope (SEM), Coulter Counter Multisizer 3 and swelling ratio analysis. The degradation profile of the HA HGPs in response to pH change was quantified by carbazole assay following Xu et al., *Biomaterials*, 33:9049 (2012). To formulate MNs-loaded HGPs, the payload was added into the HA aqueous solution prior to the inverse emulsion crosslinking process.

Formulation of MS containing HA HGPs: Poly(butyl methacrylate-co-(2-dimethylaminoethyl) methacrylate-co-methyl methacrylate) ("EPO") was used as the polymer to formulate the MS. The formulation was conducted via a solvent evaporation technique. The developed EPO-MS-HGPs were characterized by SEM as well as confocal microscopy through the fluorescent labeling of HGPs.

Release studies of MNs from EPO-MS-HGPs: The release study was performed under three different conditions: (1) in water at RT; (2) in SGF at 37° C.; and (3) in water at 100° C. The release of the MNs was quantified using UV-Vis spectrometer or ELISA.

Results and Discussion

A delivery platform consisting of a hyaluronic acid (HA) hydrogel particle (HGP)-based core for MNs encapsulation, and a low-pH-soluble and thermostable microsphere (MS) jacket surrounding the HGPs for protection purposes was developed. The MS jacket is encased by sodium chloride, yielding MNs fortified salt. The developed system is shown to efficiently encapsulate MNs, maintain their stability under cooking conditions, and release the payload in simulated gastric fluid (SGF) with desired release profiles. This polymeric particle platform has great potential for MNs fortification of salt.

Preparation of HA HGPs: HGPs with sizes of 4±2 µm and 19±7 µm were formulated by the inverse emulsion method. Particle size obtained by SEM and Coulter Counter are in good agreement with each other. The swelling ratios of the HGPs were measured as 23±3 µm and 20±4 µm, respectively. The HGPs were stable in water, however, a 58±4% of weight loss was obtained by immersing the HGPs in SGF for 2 hr.

Formulation of MS containing HA HGPs: EPO-MS-HGPs with an average size of 200 µm were formulated by solvent evaporation. HA HGPs were homogeneously distributed within the EPO-based microspheres. The distribution of HGPs within MS was also revealed by SEM and confocal microscopy.

Release studies of MNs from EPO-MS-HGPs: Limited release of MNs was found when EPO-MS-HGPs were immersed in water at both RT and 100° C. In contrast, complete release of MNs was obtained in SGF at 37° C. after the dissolution of EPO and the hydrolytical degradation of the HGPs.

Conclusions

A pH responsive polymeric delivery system was developed and characterized. The platform could encapsulate various types of MNs for salt fortification.

Example 5

Hydrogel Particle Characterization and Release Properties

Materials and Methods

Representative mineral NaFeEDTA and representative vitamin, Vitamin B12, were encapsulated within particles formed as described in Example 4 using the hyaluronic acid derivatives described in scheme 1 above, HA-CHO and HA-HYZ.

The hydrogel particles were characterized for release over time at room temperature and 37° C., in water and in simulated gastric fluid.

The particles were then encapsulated in EPO, as shown below:

Scheme 2

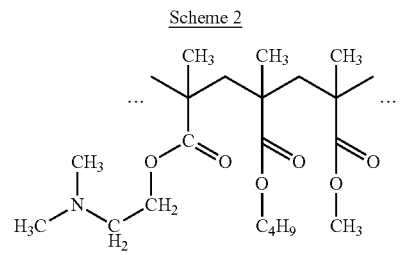

EPO refers to a commercially available cationic copolymer formed of butyl methacrylate, dimethylaminoethyl methacrylate, and methyl methacrylate. The proper IUPAC name is poly(butyl methacrylate-co-(2-dimethylaminoethyl) methacrylate-co-methyl methacrylate). The chemical structure in Scheme 2 shows the above repeat units that make up EPO.

Results

TABLE 2

Properties of HA Derivatives and Resulting Particles.

|  | Mw* (KDa) | Mn* (KDa) | PDI* | SD** |
|---|---|---|---|---|
| HA-HYZ | 764 | 346 | 2.2 | 37 |
| HA-CHO | 609 | 304 | 2.0 | 65 |

| Sample | Emulsifying speed (rpm) | Particle size | Swelling ratio |
|---|---|---|---|
| HGP4 | 1500 | 4 ± 2 | 23 ± 3 |
| HGP19 | 500 | 19 ± 7 | 20 ± 4 |

*Determined by GPC.
**SD: degree of substitution, determined by $^1$H NMR or Iodometry.

Figure 9:
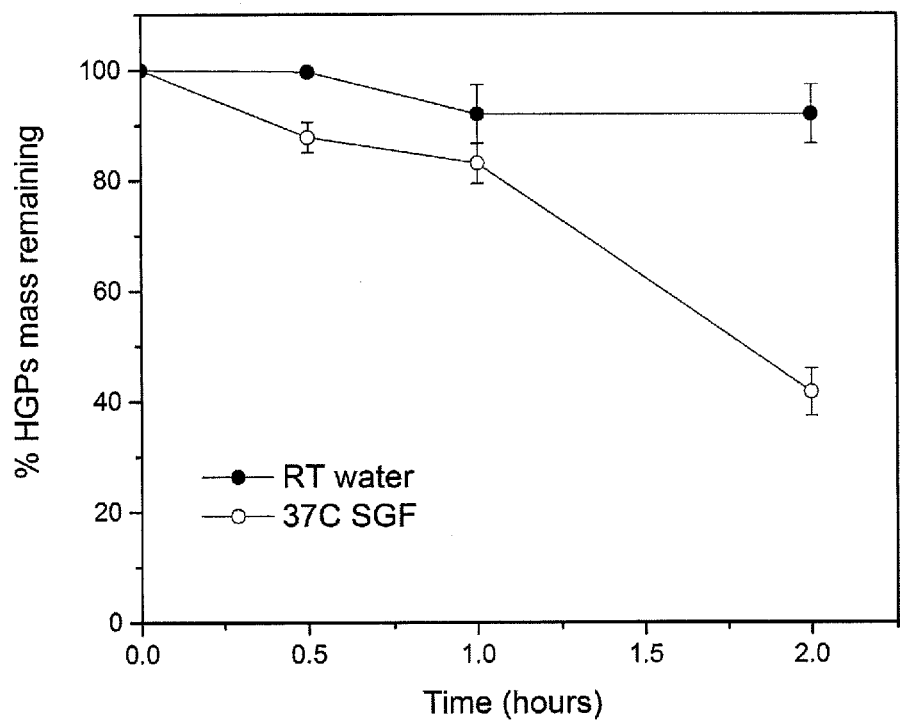
FIG. 9 is a graph of the hydrolytic stability of the HA hydrogel particles. The gel mass as a function of incubation time at room temperature in water or at 37° C. in simulated gastric fluid was compared over time in hours.

The hydrolytic stability of the HA hydrogel particles is shown in FIG. 9. The gel mass as a function of incubation time at room temperature in water or at 37° C. in simulated gastric fluid was compared over time in hours.

Figure 10A:
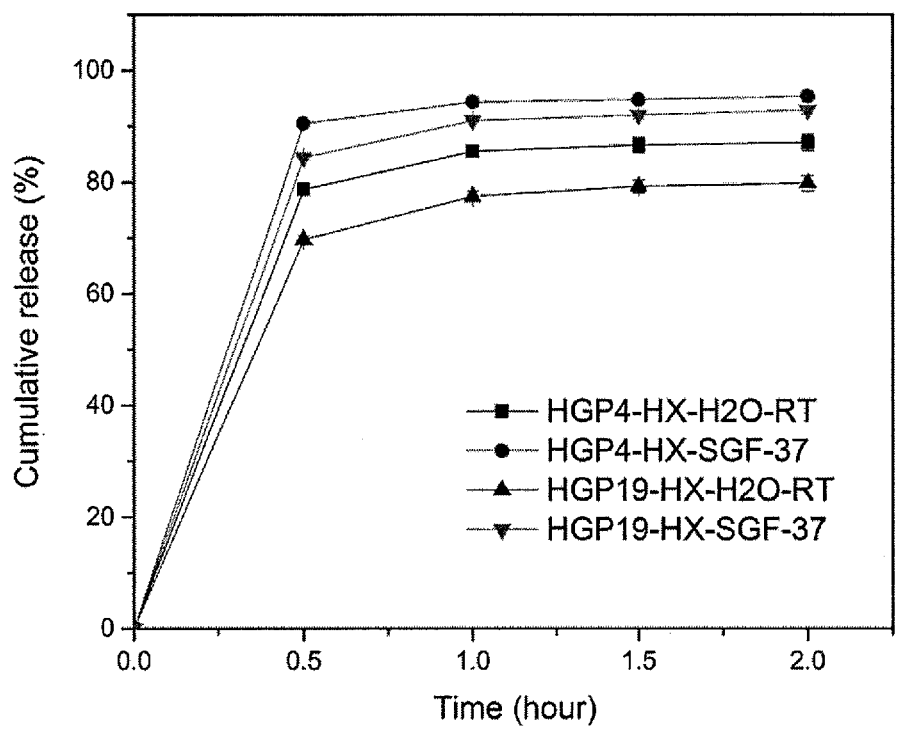
FIGS. 10A and 10B are graphs showing the cumulative in vitro release of a representative mineral, NaFeEDTA (FIG. 10A), and a representative vitamin, Vitamin B12 (FIG. 10B), from the hydrogel particles over time in hours.
Figure 10B:
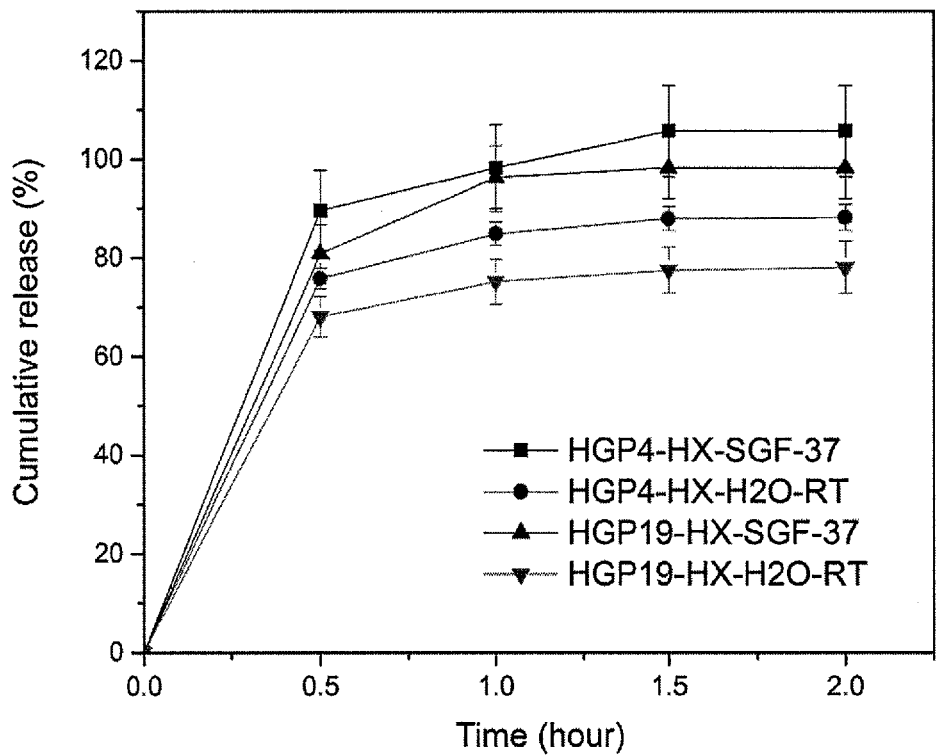

FIGS. 10A and 10B are graphs showing the cumulative in vitro release of a representative mineral, NaFeEDTA, and a representative vitamin, Vitamin B12, from the hydrogel particles over time in hours.

Factors that affect the size of the particles include stirring speed, amount of surfactant, polymer concentration, ratio between organic solvent (polyvinyl alcohol, PVA) and non-solvent (water), and temperature. 10 mg/ml PVA produced 200 micron particles and 50 mg/ml PVA produced 25 micron particles.

SEM shows the particles were stable at 100° C. for two hours. SEM, light microscopy and confocal microscopy showed that the hydrogel particles were homogenously distributed with the EPO microspheres.

Figure 11A:
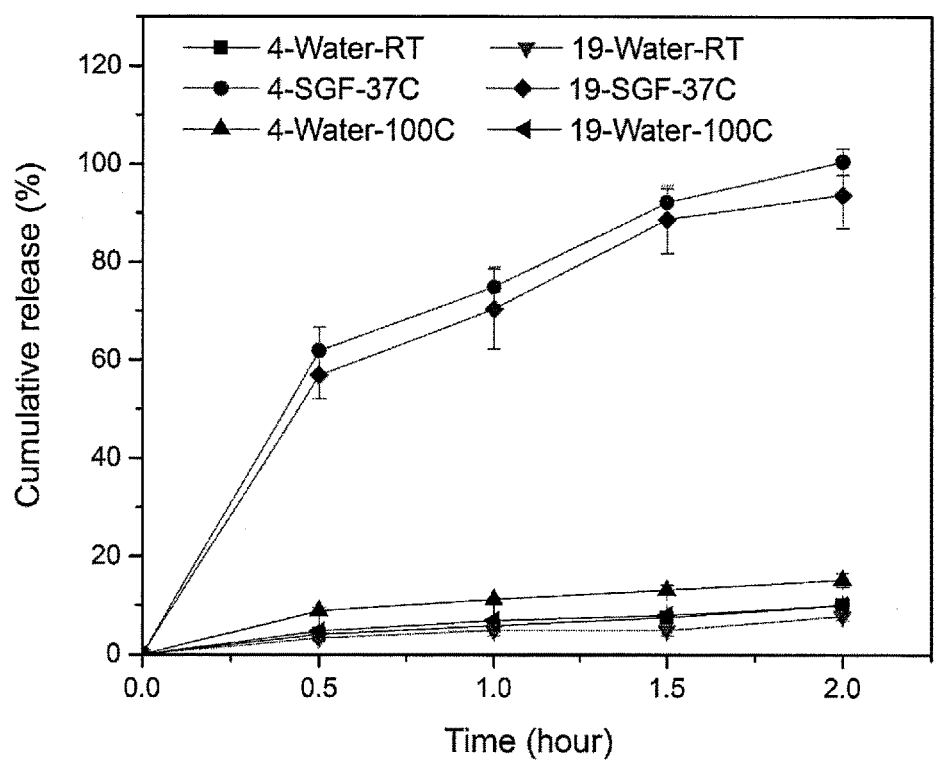
FIGS. 11A and 11B are graphs showing cumulative release of the micronutrients, NaFeEDTA (FIG. 11A) and vitamin B12 (FIG. 11B), from the EPO-HA hydrogel microspheres at room temperature in water, 37° C. in simulated gastric fluid and 100° C. in water, over time in hours.
Figure 11B:
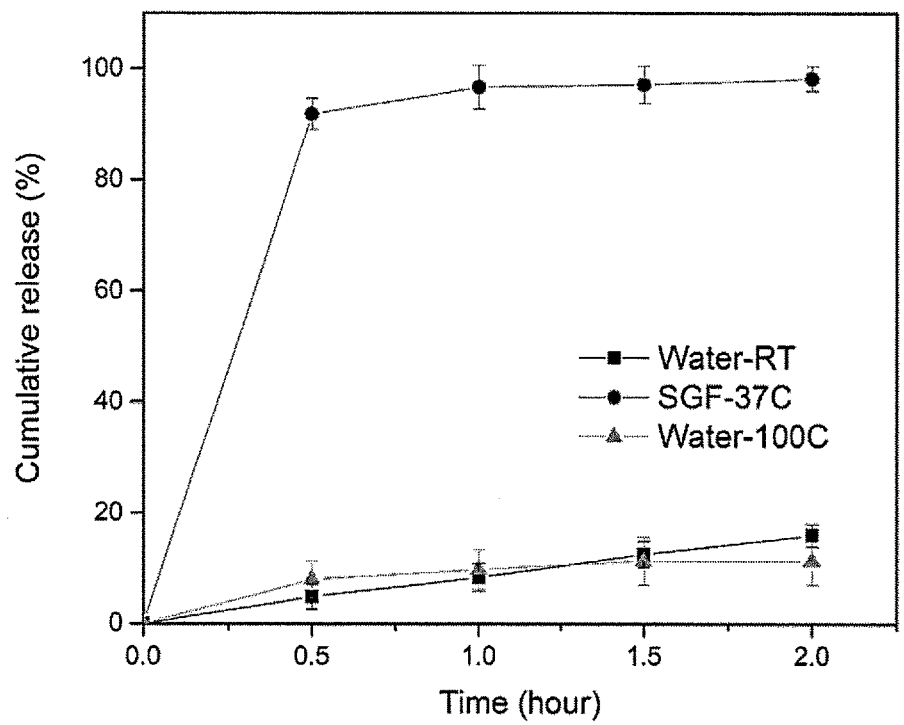

Release of the micronutrients, NaFeEDTA and vitamin B12, from the EPO-HA hydrogel microspheres is shown in FIGS. 11A and 11B at room temperature in water, 37° C. in simulated gastric fluid and 100° C. in water, over time in hours.

Example 6

Micronutrient Encapsulation and Release Studies

Materials and Methods

Eight essential micronutrients, presented in Table 3, were encapsulated and their release studied in vitro.

The micronutrient iron is used in two forms, iron-EDTA (NaFeEDTA) and iron sulfate (FeSO4). Iron-EDTA is a stable form of iron, but at high doses the formulation may deliver too much EDTA for small children. Incorporation of iron sulfate into the formulation is safer for the children.

TABLE 3

Micronutrient Recommended Daily Values for some groups (source: Institute of Medicine)

| Micronutrient | Forms | Women 19-30 yrs (mg/day) | Pregnant women 19-30 yrs (mg/day) | Lactating women 19-30 yrs (mg/day) | Children 1-3 yrs (mg/day) |
|---|---|---|---|---|---|
| Iron | NaFeEDTA/FeSO$_4$ | 18 | 27 | 18 | 7 |
| Zinc | Zinc oxide | 8 | 11 | 12 | 3 |
| Vitamin A | Retinyl Palimitate (dry) | 0.70 | 0.77 | 1.3 | 0.30 |
| Vitamin B9 | Folic acid | 0.4 | 0.6 | 0.5 | 0.15 |
| Vitamin B12 | Vitamin B12 | 0.0024 | 0.0026 | 0.0028 | 0.0009 |
| Vitamin C | Ascorbic acid | 75 | 85 | 120 | 15 |
| Vitamin D | Vitamin D3 | 0.015 | 0.015 | 0.015 | 0.015 |
| Iodine | Potassium iodide | 0.15 | 0.22 | 0.29 | 0.09 |

In-house assays were developed for micronutrient detection and determination of encapsulation efficiency and release kinetics. A summary of micronutrient detection methods is presented in Table 4 below.

Figure 12A:
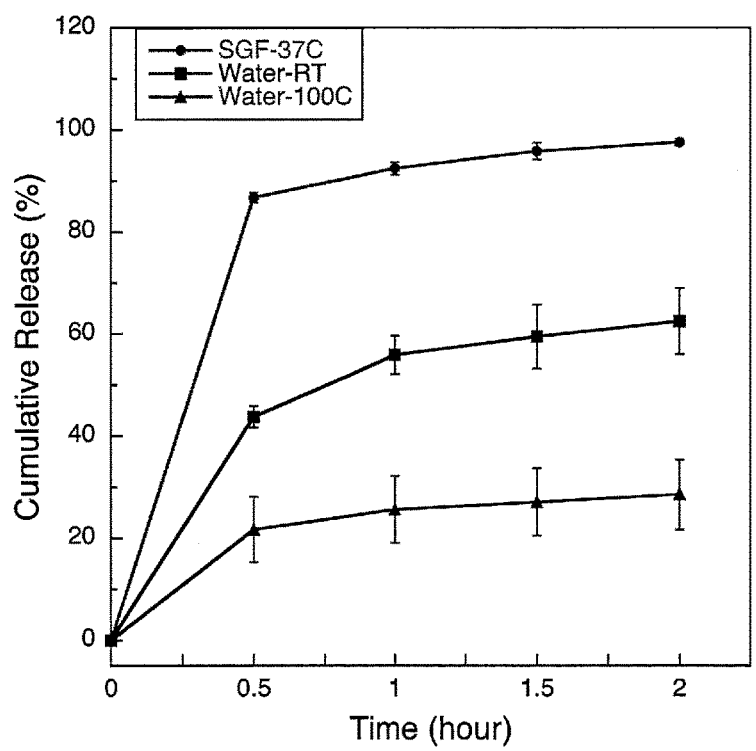
FIGS. 12A and 12B are graphs showing cumulative release (%) of the micronutrient $KIO_3$ from the EPO-microspheres at room temperature in water, 37° C. in simulated gastric fluid and 100° C. in water, over time in hours. The EPO-microspheres were formed using either 100 mg/ml EPO (FIG. 12A), or 200 mg/ml (FIG. 12B).
Figure 12B:
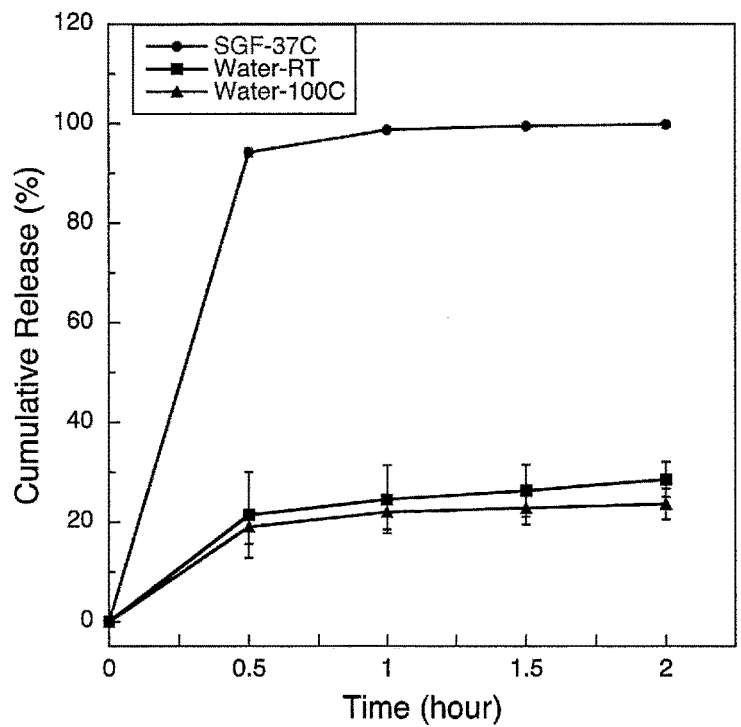

Iodine was encapsulated at 75.2±8.9% efficiency, with iodine loading per mg of EPO of 21.2±2.5 μg. Iodine, delivered in the form of potassium iodide (KIO$_3$) was directly encapsulated into the EPO-MS through a solid/oil/water process. EPO100: 100 mg/ml EPO used for emulsion (FIG. 12A); EPO200: 200 mg/ml EPO used for emulsion (FIG. 12B).

Vitamin A was encapsulated at 31.3±5.0% efficiency, with vitamin A loading per mg of EPO of 7.4±1.2 μg. Vitamin A was directly mixed with EPO in dichloromethane (DCM) and was encapsulated in the EPO-microspheres.

TABLE 4

A summary of micronutrient detection assays and detection ranges.

| Micronutrients | Methods | Detection Range |
|---|---|---|
| Iodate (KIO$_3$) | UV-Vis | 0-12.5 μg/ml |
| Iron (NaFeEDTA) | UV-Vis | 0-50 μg/ml |
| Iron (FeSO$_4$) | Calorimetric | 0-100 μmol |
| Zinc (ZnSO$_4$) | Calorimetric | 0-4 nmol |
| Vitamin A | UV-Vis | 0-300 μg/ml |
| Vitamin B9, folic acid | UV-Vis | 0-400 ng/ml |
| Vitamin B12 | UV-Vis | 0-40 ng/ml |
| Vitamin C | Calorimetric | 0-10 nmol |
| Vitamin D3 | UV-Vis | 0-300 μg/ml |

Vitamin D3 was encapsulated at 79.9±7.4% efficiency, with vitamin D3 loading per mg of EPO of 19.8±1.8 μg. Vitamin D3 was directly mixed with EPO in DCM and was encapsulated in the EPO-microspheres.

Vitamin C was encapsulated at 11.95±0.65% efficiency, with vitamin C loading per mg of EPO of 13.75±0.75 μg. Vitamin C was directly mixed with EPO and encapsulated in the EPO-microspheres.

Vitamin B9 (folic acid) was encapsulated into EPO-gelatin microspheres at 51.4±3.3% efficiency, with vitamin B9 loading per mg of EPO of 1.66±0.11 μg.

Results

KIO$_3$ was steadily released in simulated gastric fluid (SGF) environment at 37° C., and an increase in the EPO concentration reduced the leakage of the KIO$_3$. Also, the EPO-MS containing KIO$_3$ were stable at 100° C. in water during the two hour incubation time (FIGS. 12A and 12B), with a cumulative release of KIO$_3$ of about 20%. Higher concentration of EPO reduced the leakage of KIO$_3$.

Figure 13:
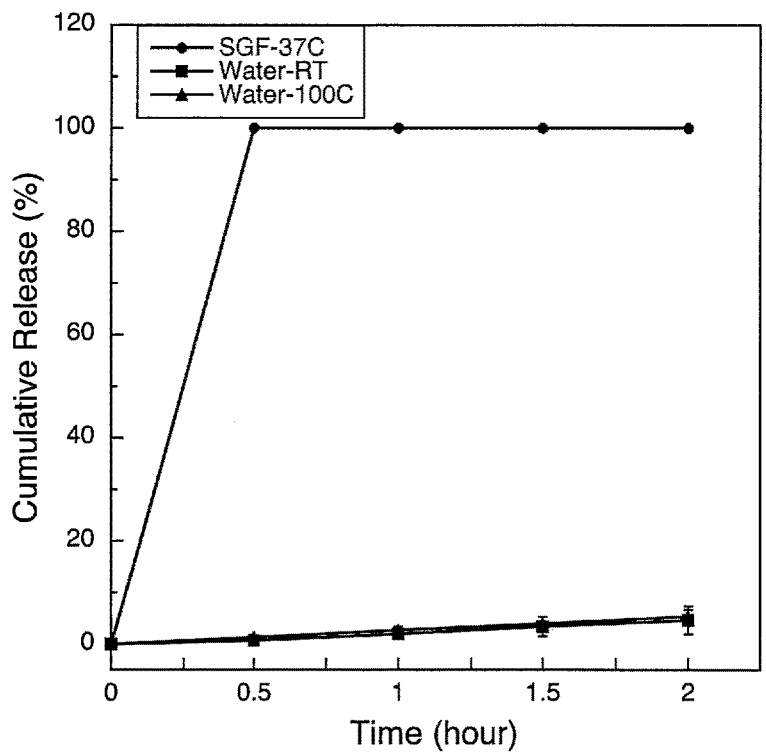
FIG. 13 is a graph showing cumulative release (%) of the micronutrient vitamin A from the EPO-microspheres at room temperature in water, 37° C. in simulated gastric fluid and 100° C. in water, over time in hours.

Vitamin A-encapsulated EPO-MS showed limited release of the vitamin in room temperature and at 100° C. in water. Complete release of vitamin A was obtained in SGF at 37° C. (FIG. 13).

Figure 14:
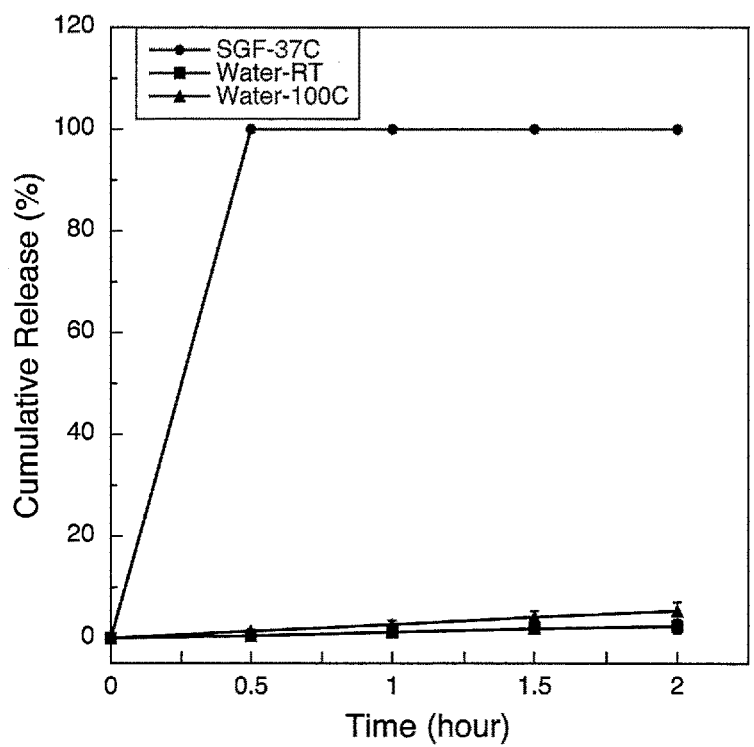
FIG. 14 is a graph showing cumulative release (%) of the micronutrient vitamin D3 from the EPO-microspheres at room temperature in water, 37° C. in simulated gastric fluid and 100° C. in water, over time in hours.

Fast and complete release of vitamin D3 in SGF at 37° C. and slow and limited release in water at room temperature and 100° C. was observed (FIG. 14).

Figure 15:
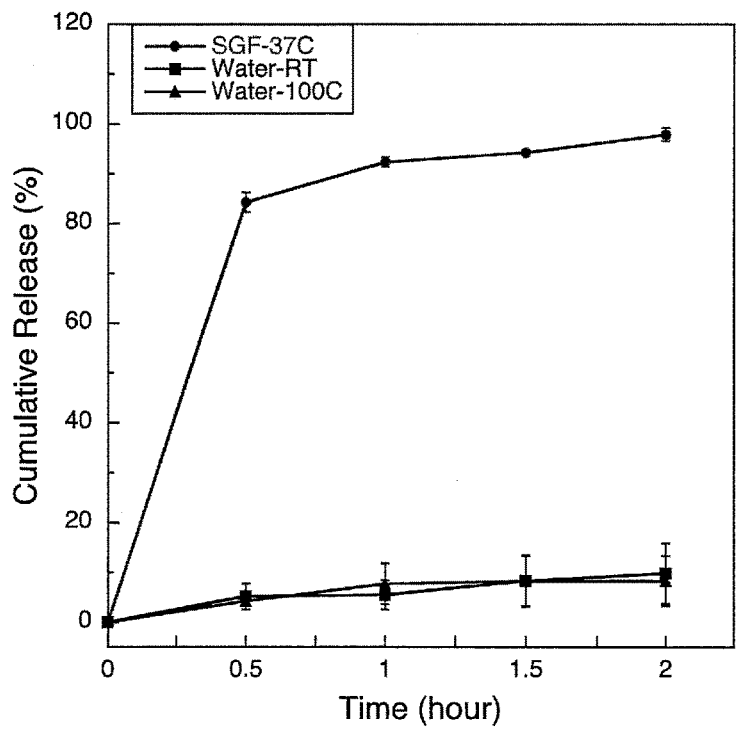
FIG. 15 is a graph showing cumulative release (%) of the micronutrient vitamin C from the EPO-microspheres at room temperature in water, 37° C. in simulated gastric fluid and 100° C. in water, over time in hours.

Limited release of vitamin C was found at both room temperature and 100° C. boiling water after two hours. Complete release of vitamin C was observed in SGF at 37° C. after 0.5 hours (FIG. 15).

Figure 16:
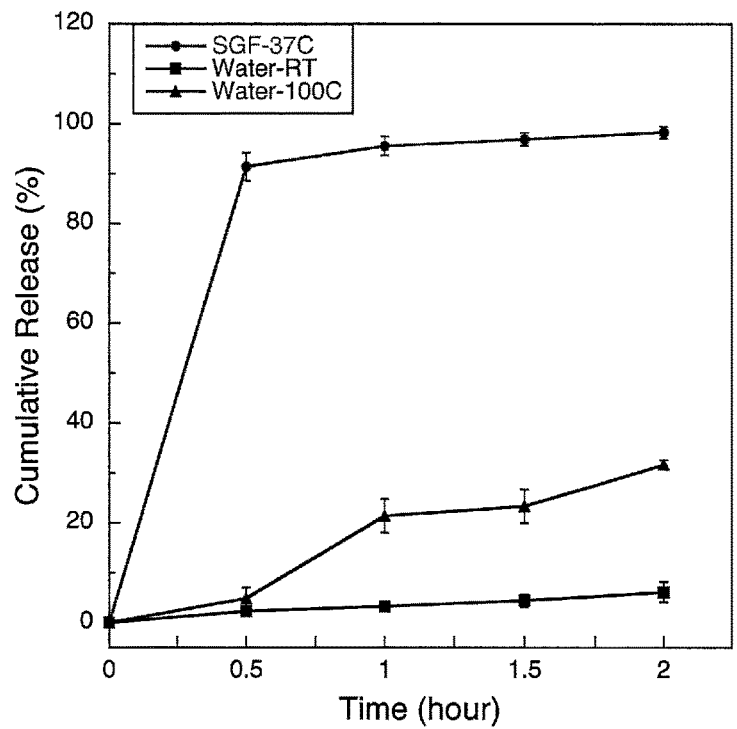
FIG. 16 is a graph showing cumulative release (%) of the micronutrient vitamin B9 (folic acid) from the EPO-gelatin-microspheres at room temperature in water, 37° C. in simulated gastric fluid and 100° C. in water, over time in hours.

Limited release of vitamin B9 was found at room temperature after two hours. Slight leakage was found at 100° C. boiling water after two hours. Complete release of vitamin B9 was observed in SGF at 37° C. after 0.5 hours (FIG. 16).

The addition of 1% oil during boiling did not increase release of vitamin B12 after two hours.

Example 7

Coating of Polymer Matrix with Salts

Materials and Methods

Various compositions were tested for their ability to bind salt crystals to each other and to a surface of beads. A homogenous solution of a binder composition and NaCl (200 mg/ml) in water was prepared using wheat starch (0.5 dry wt %), corn starch (0.5 dry wt %), potato starch (0.1 dry wt %), polyvinyl alcohol (PVA) (1 dry wt %), carboxymethyl cellulose (1 dry wt %), or methyl cellulose (1 dry wt %) as binders. The solutions were dried at 100° C. on watch glasses and the morphology and flexibility of the resulting films were compared.

Polystyrene beads were used as a model particle to demonstrate salt coating. Hydrophobic dye labeled polystyrene (PS) beads were salt coated either by suspending the PS beads in NaCl/binder solution and allowing them to dry at 100° C. in the oven overnight, or by using fluid bed coating. Fluidized bed was performed under controlled condition and in large scale (1 L in volume) using carboxymethyl cellulose (4 mg/ml) and NaCl (200 mg/ml). Fluid bed inlet temperature was 200° F., coating yield was 97.6 wt %. Coating thickness could be tuned by adjusting the concentration of the coating materials.

Results

Based on the morphology and flexibility of the obtained binder/salt films, carboxymethyl cellulose and corn starch were selected as the preferred binders for salt coating.

The coating experiments of PS beads demonstrated that fluid bed was a feasible approach for salt coating. The fluid bed approach allowed for homogenous coating of PS beads to even thickness with salt using carboxymethyl cellulose as a binder (FIG. 18A). The thickness of the salt coating layer was 135 µm. The coating thickness can be tuned by adjusting the concentration of the coating materials.

Summary

HA (modified and unmodified), gelatin, and EPO microspheres (MS) were formulated by an emulsion method. The size of the particles can be easily adjusted by changing the concentration of the surfactant, the speed of stirring, etc. The successful incorporation of HA and gelatin particles into the EPO-MS was demonstrated by light microscope, SEM and confocal microscope analysis. The formulated EPO-HA-MS and EPO-gelatin-MS are stable in boiling water for at least 2 hr. Micronutrients (8 critical ones) were easily encapsulated. Limited (<20%) MNs leakage was found by immersing the particle in water at both room temperature and boiling water for 2 hr. In contrast, complete release of the MNs was found when the particles were immersed in SGF (pH 1.2) after 2 hr. Homogeneous salt (NaCl) layer was successfully coated onto the surface of the PS beads (used as a model). Pharmaceutical binders were used to aid the coating.

The developed EPO formulations were demonstrated to protect the MNs under cooking conditions and release them in the stomach. Fluidized bed was demonstrated as a technique to be used for salt coating.

Example 8

Stability Studies

Formulations were tested for factors that increase stability and leakage characteristics for particular nutrients.

Vitamin C

By increasing the concentration of the polymer coating, the release of ascorbic acid during cooking at 100° C. was significantly reduced and the recovery of ascorbic acid was significantly increased. Ascorbic acid can become oxidixed and hydrolyzed, resulting in reduced bioactivity. Compounds specifically identified as stabilizing ascorbic acid, trans-Ferulic Acid (FA), Caffeic Acid (CA), and p-Coumaric Acid (p-CA), can be used in the particles and matrix to stabilize vitamin C. Tests with trans-Ferulic Acid (FA) and p-Coumaric Acid (p-CA) demonstrated that the recovery of ascorbic acid was significantly increased after 100° C. for two hours when they were included in the formulation. Increasing the concentration of ascorbic acid (1 mg/ml versus 78 µg/ml) also greatly increased its stability and recovery after cooking.

To increase the loading of the ascorbic acid in the formulations, large amounts of ascorbic acid need to be added in the initial formulation process. However, the use of large amount of ascorbic acid can lower the pH of the water during the formulation, and this low pH condition can also dissolve the polymer we use to make the microparticles. To avoid this low pH issue, sodium ascorbate, which has equivalent bioactivity as ascorbic acid, can be used. Over 60 wt % of sodium ascorbate (NaAA) can be recovered after 2 hrs heating at 100° C. The increase of vitamin C's loading content can significantly improve its stability under cooking condition (Table 5).

TABLE 5

Increase Vitamin C (sodium ascorbate) Concentration/Loading Content

| NaAA for EPO-MS formulation (mg) | EPO (mg) | NaAA Loading per mg EPO-MS (µg) | NaAA Encapsulation efficiency (%) | % Recovery after 100° C. |
|---|---|---|---|---|
| 100 | 200 | 117.05 ± 4.48 | 35.11 ± 1.34 | 59.90 ± 1.53 |
| 200 | 200 | 132.51 ± 0.69 | 26.50 ± 0.14 | 66.22 ± 1.37 |
| 50 | 200 | 123.31 ± 2.38 | 61.66 ± 1.19 | 72.01 ± 1.15 |

Vitamin D3

Vitamin D3 is not stable under heat. Alteration involves ring-closure that allows generation of pyro- and isopyro-isomers. Our study shows that vitamin D3 is stable in water at room temperature, as well as in acidic condition, SGF (pH=1.2) at 37° C. However, it degraded in water at 100° C. after 2 hours. The recovery of vitamin D3 in water at 100° C. is concentration-dependent. When the starting amount of vitamin D3 increased, the recovery after 2 hours cooking also went up, from 2% (15 μg), to 12% (60 μg), to 40% (240 μg), and to 60% (1 mg). The encapsulation of vitamin D3 in EPO matrix helped to stabilize the vitamin D3. The characteristic absorbance peak of vitamin D3 was preserved in D3-EPO after 100° C. in water for 2 hours. In comparison, vitamin D3 itself in the same condition totally degraded (from UV spectrum result). With HPLC, the recovery of D3 in D3-EPO was quantified to be around 47%. As a conclusion, encapsulation of vitamin D3 in EPO matrix dramatically increased the stability of vitamin D3 under cooking conditions (100° C. for 2 hours).

Vitamin B12

Vitamin B12 was encapsulated in the EPO-HA microspheres and subjected to autoclaving. The autoclaving conditions were 16 psig and 250° F. for 30 minutes. No severe leakage of vitamin B12 was found. Thus, the formulations can survive and prevent the leakage of MNs under autoclaving conditions.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A salt formulation comprising:
   particles comprising one or more therapeutic agents, prophylactic agents, nutraceutical agents, diagnostic agents, or combinations thereof,
   a matrix formed of inert excipient having the particles dispersed therein,
   a pH-sensitive polymer coating on the outer surface of, or surrounding, the matrix,
   wherein the composition, thickness and concentration of the pH sensitive polymer coating is effective to resist permeation of water into the matrix and prevent oxidation of the agents for one hour at 100° C., and provides release of the particles upon exposure to a pH and temperature in the gastrointestinal tract but not at a higher pH,
   wherein the formulation is stable up to one hour at 100° C., and
   a coating of one or more salts on the pH-sensitive polymer coating,
   wherein the coating comprises between about 10 and 80% by weight of one or more salts selected from the group consisting of sodium or potassium chloride, magnesium chloride, potassium iodide, phosphates, and combinations thereof.

2. The formulation of claim 1, wherein the particles comprise vitamins, trace minerals, micronutrients, or combinations thereof.

3. The formulation of claim 1, wherein the matrix is partially or wholly formed of materials selected from the group consisting of salts, sugars, carbohydrates, oils, fats, waxes, proteins, and combinations thereof.

4. The formulation of claim 1, wherein the matrix is partially or wholly formed of a hydrogel.

5. The formulation of claim 4, wherein the hydrogel is formed of one or more polymers selected from the group consisting of hyaluronic acid, cyclodextrin, collagen, alginate, chitin, polyethylene glycol and copolymers thereof, ethylene glycol dimethacrylate, hydroxyethyl methacrylate, poly(butylene oxide), polycaprolactone, poly(ethylene oxide) and copolymers thereof, poly(ethylene imine), poly(ethyl methacrylate), propylene fumarate, poly(hydroxy butyrate), poly(hydroxyethyl methacrylate), poly(hydroxypropyl methacrylamide), poly(lactic acid), poly(lactic-co-glycolic acid), poly(N-vinyl pyrrolidone), poly(propylene oxide), poly(vinyl alcohol), poly(vinyl acetate), and poly(vinyl amine).

6. The formulation of claim 1, wherein the polymer coating comprises one or more pH-sensitive polymers that dissolve at a pH between about 1 and 5.

7. The formulation of claim 1, wherein the polymer coating comprises one or more pH-sensitive polymers that dissolve at a pH between about 5 and 8.

8. The formulation of claim 1, comprising pH-sensitive polymer selected from the group consisting of cationic polymers, polymers that become cationic under physiological conditions, and combinations thereof.

9. The formulation of claim 1, comprising pH-sensitive polymer selected from the group consisting of polymethacrylates containing functional groups that form salts at a pH greater than 5.0, naturally occurring cellulosic polymers, polysaccharides, polyvinyl acetate phthalate, shellac, fatty acids, waxes, plastics, plant fibers, and combinations thereof.

10. The formulation of claim 2, wherein the vitamins, trace minerals, and micronutrients are selected from the group consisting of iron, zinc, manganese, copper, iodine, selenium, molybdenum, chromium, vitamin A, vitamin B1, vitamin B2, vitamin B3, vitamin B6, vitamin B9 (folic acid), vitamin B12, vitamin C, vitamin D3, vitamin E, vitamin K, pantothenic acid, biotin, and combinations thereof.

11. The formulation of claim 1 further comprising antiparasitic agents.

12. The formulation of claim 11, wherein the anti-parasitic agents are selected from the group consisting of antinematodes, anticestodes, antitrematodes, antiamoebics, antiprotozoals, and combinations thereof.

13. The formulation of claim 12, wherein the antinematodes are selected from the group consisting of mebendazole, pyrantel pamoate, thiabendazole, diethylcarbamazine, ivermectin, and combinations thereof.

14. The formulation of claim 12, wherein the anticestodes are selected from the group consisting of niclosamine, praziquantel, albendazole, and combinations thereof.

15. The formulation of claim 1, wherein the pH sensitive polymer is a copolymer formed of butyl methacrylate, dimethylaminoethyl methacrylate, and methyl methacrylate.

16. A method of providing salt, trace minerals, vitamins, micronutrients, or combinations thereof, the method comprising providing an effective amount of the formulation of claim 1 to an individual in need thereof.

17. The method of claim 16, wherein the formulation is provided for cooking.

18. The method of claim 16, wherein the formulation is provided in bulk form to agricultural animals.

* * * * *